(12) United States Patent
Blatter et al.

(10) Patent No.: US 6,626,921 B2
(45) Date of Patent: *Sep. 30, 2003

(54) EXTERNALLY POSITIONED ANVIL APPARATUS FOR CUTTING ANASTOMOSIS

(75) Inventors: Duane D. Blatter, Salt Lake City, UT (US); Kenneth C. Goodrich, Salt Lake City, UT (US); Michael C. Barrus, Centerville, UT (US); Bruce M. Burnett, Salt Lake City, UT (US); Nemo J. Tullius, Salt Lake City, UT (US)

(73) Assignee: Integrated Vascular Interventional Technologies, L.C., Salt Lake City, UT (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 10/003,956

(22) Filed: Oct. 31, 2001

(65) Prior Publication Data

US 2002/0038127 A1 Mar. 28, 2002

Related U.S. Application Data

(63) Continuation-in-part of application No. 09/736,781, filed on Dec. 14, 2000, now Pat. No. 6,551,334, which is a continuation-in-part of application No. 09/460,740, filed on Dec. 14, 1999, which is a continuation-in-part of application No. 09/293,366, filed on Apr. 16, 1999.

(51) Int. Cl.[7] .............................................. A61B 17/32
(52) U.S. Cl. ...................... 606/153; 606/170; 606/184; 600/567
(58) Field of Search ................................ 606/153, 159, 606/170, 180, 184; 600/567

(56) References Cited

U.S. PATENT DOCUMENTS

| 1,052,374 | A | 2/1913  | Parr |
| 2,192,699 | A | 3/1940  | Storz |
| 2,818,852 | A | 1/1958  | Kugler .......................... 128/2 |
| 3,104,666 | A | 9/1963  | Hale et al. .................. 128/305 |
| 3,701,352 | A | 10/1972 | Bosworth ................... 128/305 |
| 3,776,237 | A | 12/1973 | Hill et al. ................... 128/305 |
| 3,837,345 | A | 9/1974  | Matar .......................... 128/305 |
| 4,018,228 | A | 4/1977  | Goosen ....................... 128/305 |
| 4,047,654 | A | 9/1977  | Alvarado |
| 4,216,776 | A | 8/1980  | Downie et al. ............. 128/305 |
| 4,233,981 | A | 11/1980 | Schomacher ................ 128/334 |
| 4,243,048 | A | 1/1981  | Griffin ........................ 128/751 |
| 4,304,236 | A | 12/1981 | Conta et al. |
| D281,721  | S | 12/1985 | Scanlan ....................... D24/28 |
| 4,603,693 | A | 8/1986  | Conta et al. |
| 4,752,024 | A | 6/1988  | Green et al. |
| 5,005,749 | A | 4/1991  | Aranyi |
| 5,047,041 | A | 9/1991  | Samuels ...................... 606/159 |
| 5,104,025 | A | 4/1992  | Main et al. |
| 5,119,983 | A | 6/1992  | Green et al. |
| 5,129,913 | A | 7/1992  | Ruppert ...................... 606/184 |
| 5,192,294 | A | 3/1993  | Blake, III ................... 606/184 |
| 5,193,731 | A | 3/1993  | Arani |
| 5,205,459 | A | 4/1993  | Brinkerhoff et al. |
| 5,271,544 | A | 12/1993 | Fox et al. |
| 5,275,322 | A | 1/1994  | Brinkerhoff et al. |

(List continued on next page.)

*Primary Examiner*—Julian W. Woo
(74) *Attorney, Agent, or Firm*—Stoel Rives LLP

(57) ABSTRACT

The present invention is directed to a cutting apparatus for cutting an opening in a vessel for subsequent anastomosis. The cutting apparatus includes an anvil, an anvil pull and a cutter. The anvil is inserted through a small incision at the anastomosis site and brought into contact with the interior wall of a vessel so that the anvil distends the wall of the vessel. The cutter is then urged against the portion of the vessel wall that is distended by the anvil to form an opening in the vessel wall.

30 Claims, 12 Drawing Sheets

U.S. PATENT DOCUMENTS

| | | | |
|---|---|---|---|
| 5,285,945 A | 2/1994 | Brinkerhoff et al. | |
| 5,292,053 A | 3/1994 | Bilotti et al. | |
| 5,314,435 A | 5/1994 | Green et al. | |
| 5,333,773 A | 8/1994 | Main et al. | |
| 5,350,104 A | 9/1994 | Main et al. | |
| 5,392,979 A | 2/1995 | Green et al. | |
| 5,395,030 A | 3/1995 | Kuramoto et al. | |
| 5,465,895 A | 11/1995 | Knodel et al. | |
| D372,310 S | 7/1996 | Hartnett | D24/146 |
| 5,533,661 A | 7/1996 | Main et al. | |
| 5,609,285 A | 3/1997 | Grant et al. | |
| 5,632,433 A | 5/1997 | Grant et al. | |
| 5,643,305 A | 7/1997 | Al-Tameem | 606/180 |
| 5,669,918 A | 9/1997 | Balazs et al. | |
| 5,676,670 A | 10/1997 | Kim | |
| 5,690,662 A | 11/1997 | Chiu et al. | 606/184 |
| 5,702,412 A | 12/1997 | Popov et al. | 606/159 |
| 5,799,857 A | 9/1998 | Robertson et al. | |
| 5,817,113 A | 10/1998 | Gifford, III et al. | 606/153 |
| 5,833,698 A | 11/1998 | Hinchliffe et al. | |
| 5,868,770 A | 2/1999 | Rygaard | |
| 5,893,369 A | 4/1999 | LeMole | 606/184 |
| 5,910,153 A | 6/1999 | Mayenberger | 606/184 |
| 5,915,616 A | 6/1999 | Viola et al. | |
| 5,944,730 A | 8/1999 | Nobles et al. | |
| 5,954,735 A | 9/1999 | Rygaard | 606/153 |
| 5,976,178 A | 11/1999 | Goldsteen et al. | 623/1 |
| 5,993,464 A | 11/1999 | Knodel | |
| 6,022,367 A | 2/2000 | Sherts | 606/184 |
| 6,036,700 A | 3/2000 | Stefanchik et al. | |
| 6,036,710 A | 3/2000 | McGarry et al. | 606/184 |
| 6,050,472 A | 4/2000 | Shibata | |
| 6,053,390 A | 4/2000 | Green et al. | |
| 6,068,637 A | 5/2000 | Popov et al. | 606/159 |
| 6,080,173 A | 6/2000 | Williamson, IV et al. | 606/184 |
| 6,080,176 A | 6/2000 | Young | 606/185 |
| 6,117,148 A | 9/2000 | Ravo et al. | |
| 6,171,319 B1 | 1/2001 | Nobles et al. | 606/151 |
| 6,176,413 B1 | 1/2001 | Heck et al. | |
| 6,187,019 B1 | 2/2001 | Stefanchik et al. | |
| 6,190,396 B1 | 2/2001 | Whitin et al. | 606/144 |
| 6,190,397 B1 | 2/2001 | Spence et al. | |
| 6,193,129 B1 | 2/2001 | Bittner et al. | |
| 6,209,773 B1 | 4/2001 | Bolduc et al. | 227/176.1 |
| 6,241,743 B1 | 6/2001 | Levin et al. | 606/153 |
| 6,248,117 B1 | 6/2001 | Blatter | 606/153 |
| 6,254,617 B1 | 7/2001 | Spence et al. | |
| 6,280,460 B1 | 8/2001 | Bolduc et al. | 606/222 |
| 6,355,050 B1 | 3/2002 | Andreas et al. | 606/144 |
| 6,358,258 B1 | 3/2002 | Arcia et al. | 606/139 |
| 6,391,038 B2 | 5/2002 | Vargas et al. | |
| 6,551,334 B2 * | 4/2003 | Blatter et al. | 606/153 |
| 2002/0082614 A1 | 6/2002 | Logan et al. | |

* cited by examiner

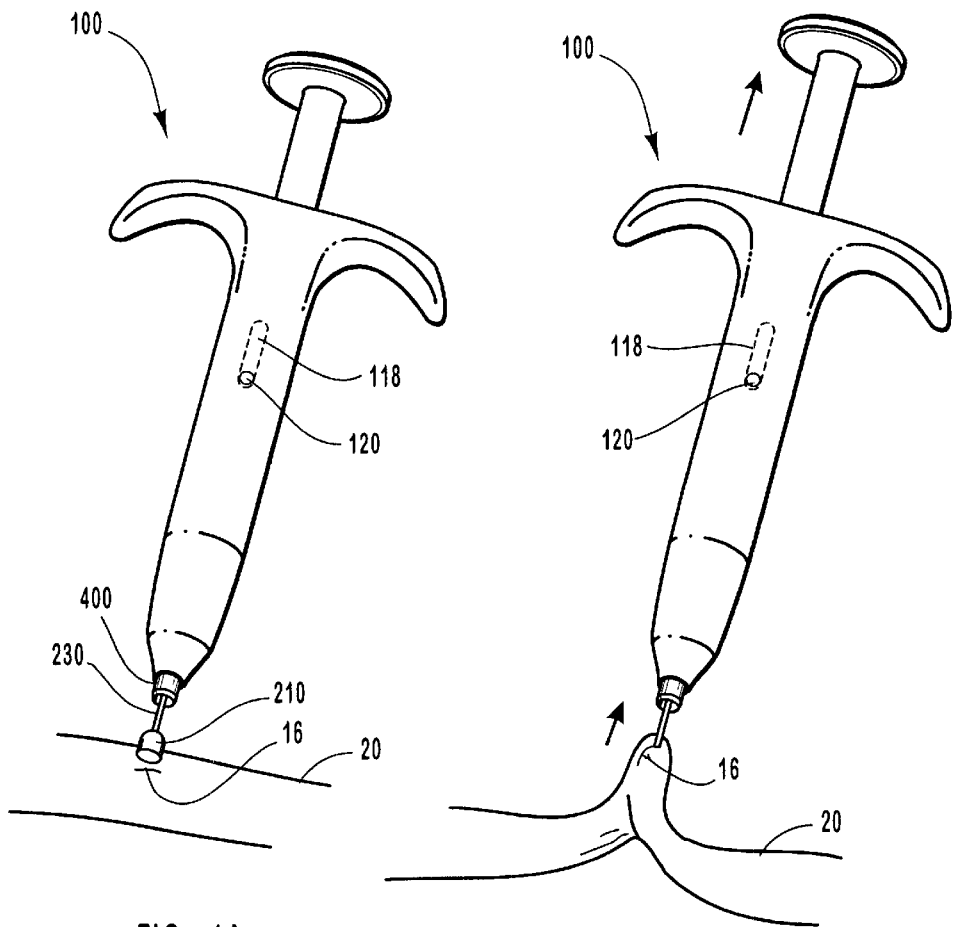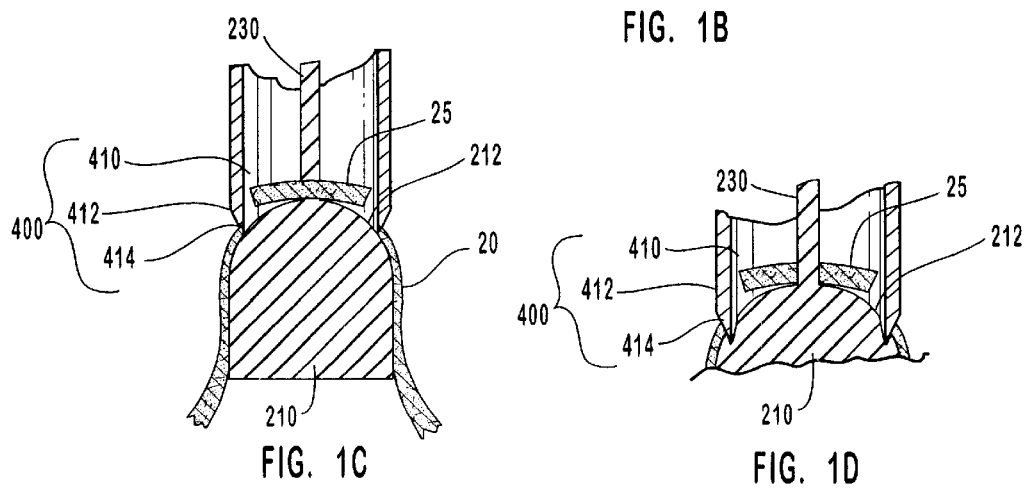
FIG. 1A
FIG. 1B
FIG. 1C
FIG. 1D

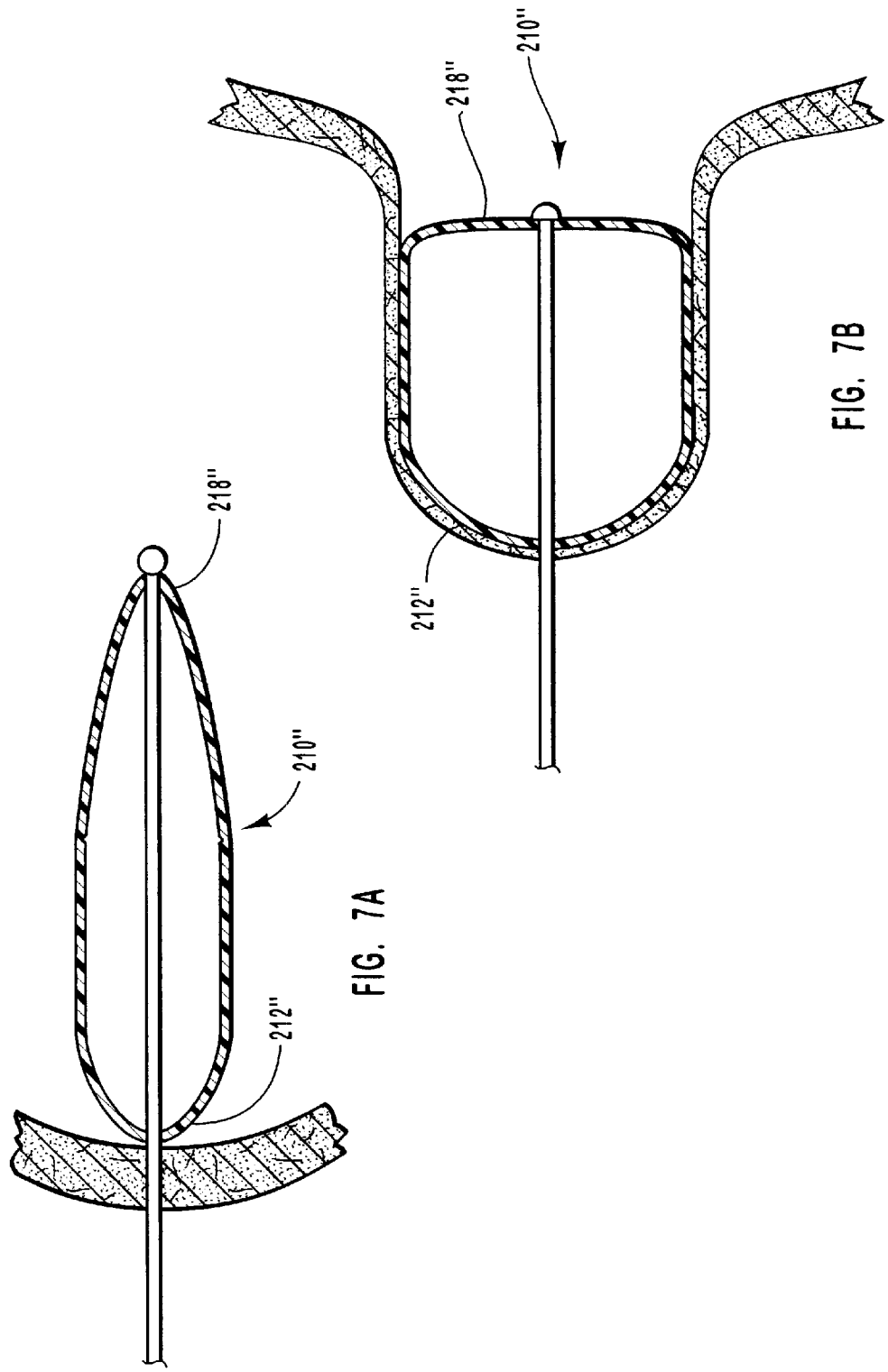

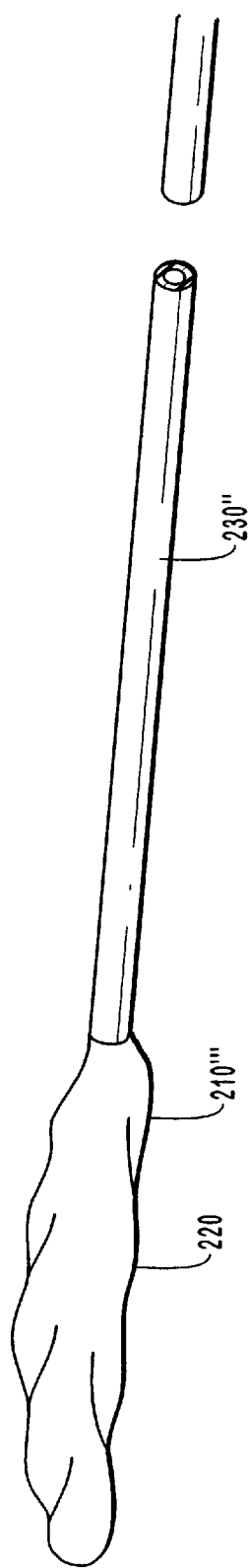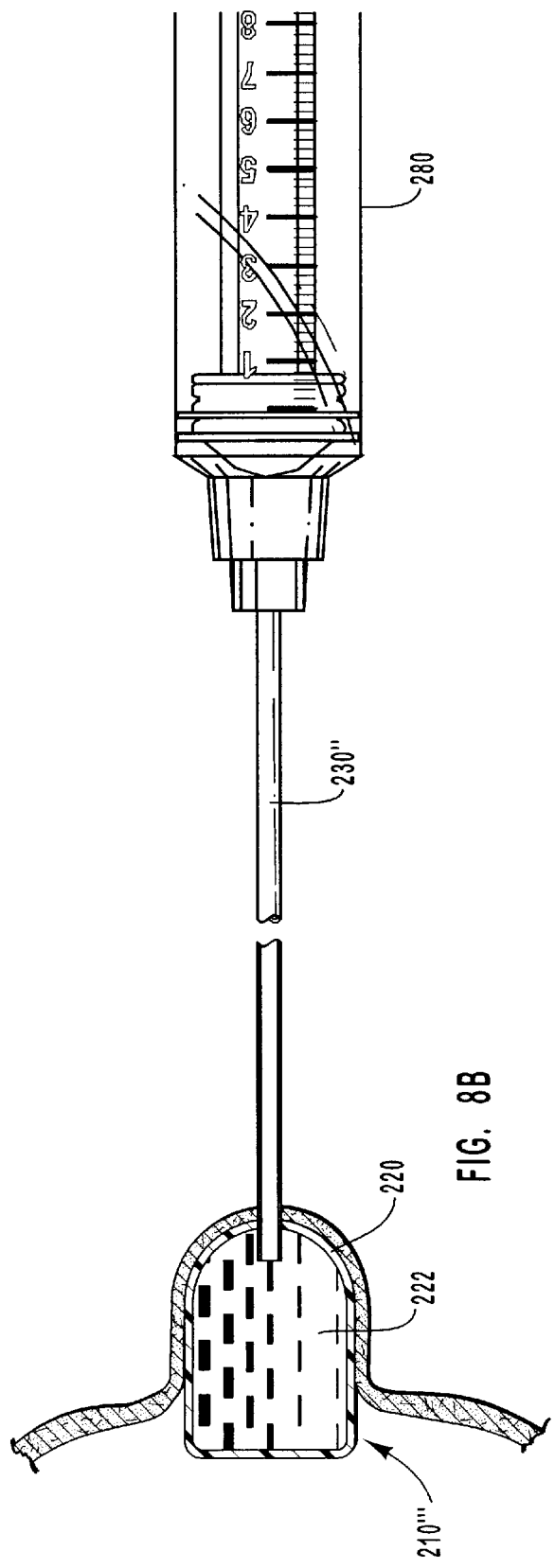
FIG. 8A
FIG. 8B

EXTERNALLY POSITIONED ANVIL APPARATUS FOR CUTTING ANASTOMOSIS

RELATED APPLICATIONS

The present application is a continuation-in-part patent application of U.S. patent application Ser. No. 09/736,781, now U.S. Pat. No. 6,551,334, entitled Externally Directed Anastomosis Systems and Externally Positioned Anastomosis Fenestra Cutting Apparatus which was filed on Dec. 14, 2000 on behalf of Duane D. Blatter, Kenneth C. Goodrich, Michael C. Barrus, Bruce M. Burnett and Nemo J. Tullius, Jr. Ser. No. 09/736,781 is a continuation-in-part patent application of U.S. patent application Ser. No. 09/460,740 entitled Compression Plate Anastomosis Apparatus which was filed on Dec. 14, 1999 on behalf of Duane D. Blatter, Kenneth C. Goodrich, Mike Barrus, and Bruce M. Burnett. The present application is also a continuation-in-part patent application of U.S. patent application Ser. No. 09/293,366 entitled Methods, Systems and Apparatus For Intraluminally Directed Vascular Anastomosis which was filed on Apr. 16, 1999 on behalf of Duane D. Blatter. Ser. Nos. 09/736,781, 09/460,740, and 09/293,366 are all incorporated herein by specific reference.

TECHNICAL FIELD

The present invention is directed generally to an anastomosis device. More specifically the present invention is directed to an externally directed apparatus for forming an opening in a vessel for subsequent anastomosis.

BACKGROUND OF THE INVENTION

An anastomosis is an operative union of two hollow or tubular structures. Anastomotic structures can be part of a variety of systems, such as the vascular system, the digestive system or the genitourinary system. For example, blood is shunted from an artery to a vein in an arteriovenous anastomosis, and from the right pulmonary artery to the superior vena cava in a cavopulmonary anastomosis. In other examples, afferent and efferent loops of jejunum are joined in a Braun's anastomosis after gastroenteroscopy; the ureter and the Fallopian tube are joined in a ureterotubal anastomosis, and the ureter and a segment of the sigmoid colon are joined in a ureterosigmoid anastomosis. In microvascular anastomosis, very small blood vessels are anastomosed usually under surgical microscope.

The operative union of two hollow or tubular structures requires that the anastomosis be tight with respect to the flow of matter through such structures and also that the anastomosed structures remain patent for allowing an uninterrupted flow of matter therethrough. For example, anastomosed blood vessels should not leak at the anastomosis site, the anastomotic devices should not significantly disrupt the flow of blood, and the anastomosis itself should not cause a biological reaction that could lead to an obstruction of the anastomosed blood vessels.

In particular, anastomosed blood vessels should ideally not develop hyperplasia, thrombosis, spasms or arteriosclerosis. Because anastomosed structures are composed of tissues that are susceptible to damage, the anastomosis should furthermore not be significantly detrimental to the integrity of these tissues. For example, injury to endothelial tissue and exposure of subintimal connective tissue should be minimized or even eliminated in vascular anastomosis. Anastomosis techniques generally intend to provide leak-proof joints that are not susceptible to mechanical failure, and they also intend to minimize damage and reduce the undesirable effects of certain operational features that may lead to post-anastomosis complications.

Optimal anastomosis requires a clean, complete opening in a vessel with minimal dangling threads of tissue. Conventional cutting techniques involve the external positioning of an anvil into the lumen of a vessel that is smaller than the cutter so that the vessel is cut as the cutter passes over the anvil. Such conventional cutting techniques operate much like a typical hand held paper punch used for forming holes by pushing a cutter over an anvil. Just like paper punches, such vascular punches often fail to fully make the cut and leave a portion attached, creating a "dangling chad" effect. The connective tissue in blood vessels in combination with the moist condition of the blood vessels further limits the effectiveness of such prior art cutting techniques. More particularly, cutting a moist highly interconnected material by squeezing it between the anvil and the cutter often results in part of the tissue merely slipping between the anvil and the cutter such that a portion is still attached. Based on the foregoing, there is a need in the art for improved methods, apparatus and systems for forming openings in vessels.

SUMMARY OF THE INVENTION

An object of the present invention is to provide an externally directed anastomosis fenestra cutting apparatus for consistently forming openings for subsequent anastomosis.

A further object of the invention is to provide a cutting device that can be reliably used to consistently form clean cuts in a vessel wall.

Still another object of the invention is to provide a device that is versatile enough to be suitably combined with a variety of vascular anastomosis techniques.

The cutting apparatus of the present invention includes an anvil, an anvil pull and a cutter. The anvil is inserted through a small incision at the anastomosis site and brought into contact with the interior wall of a vessel so that the anvil distends the wall of the vessel. The cutter is then urged against the portion of the vessel wall that is distended by the anvil to form an opening in the vessel wall.

The cutting apparatus consistently creates a complete cut having a perimeter with a desired shape such as a circle or an ellipse depending on the type of anastomosis. The precision of the cutting is due to several features. The vessel wall is distended over the anvil which enables the wall to be stretched. This assists in creating a clean cut.

The anvil is larger than the cutter so that the cut is formed due to the pressure between anvil and the cutter instead of forcing the vessel between the cutter and the anvil. The anvil has an engaging end that is preferably convex and spherical so that when engaged by a cylindrical cutter the cutter can cut against the anvil at any position in which the cutting edge is initially set against the engaging end. The cutter is also preferably spring biased which provides increased pressure for engaging the anvil.

In one embodiment, the anvil is made of a material that is softer than the material from which the cutter is made. The softer material of the anvil enables the cutter to cut into the anvil while cutting an opening into a vessel. By cutting into the anvil while cutting the vessel, the cutter is able to provide a clean cut. Alternatively, the anvil may be made of a material that is more flexible than the cutter and enables the cutter to depress the surface of the anvil inwardly when a vessel is cut. Also the anvil and cutter may be formed from materials with about the same hardness or from the same materials.

Also, the anvil is preferably configured such that it has an engaging end that is convex and is more preferably spherical so that when engaged by a cylindrical cutter the cutter can self center on the engaging end. The cutter is also preferably spring biased which provides increased pressure for engaging the anvil. The vessel wall is distended over the anvil which enables the wall to be stretched. This assists in creating a clean cut.

The ability to distend the vessel wall is particularly useful when a compression plate apparatus is utilized to join the vessels. This compression plate apparatus includes two opposing and generally annular compression plates in a generally coaxial orientation. The end of the graft vessel that is to be anastomosed is everted onto one of the compression plates. The anvil pull is used to distend the receiving vessel wall such that it extends into a compression plate apparatus. With the other compression plate placed at and around the anastomosis site, an anastomosis fenestra is opened in the wall of the receiving vessel. This anastomosis fenestra is opened within the annular region generally defined by the compression plate located at and around the anastomosis site. With the aid of the anvil of this invention, the contour of the anastomosed fenestra is engaged with the compression plate which opposes the compression plate that carries the graft vessel. This engagement is preferably accomplished with the aid of holding tabs or other similar features protruding from the compression plate placed around the anastomosis fenestra.

The degree to which the anvil has distended the receiving vessel before formation of the fenestra determines the size of the portion defining the vessel opening that remains in the compression plate apparatus. By adequately distending the receiving vessel wall, the portion defining the opening can be captured by the compression plate apparatus and everted. The graft vessel is subsequently approached to the anastomosis fenestra by reducing the separation between the compression plates, so that the graft vessel causes the eversion of the contour of the anastomosis fenestra by appropriately sliding on the surface of the anvil. Once the portion of the vessel that defines the opening has been everted then the compression plate apparatus can be compressed in a manner such that the everted portion of the receiving vessel is held against the everted portion of the other vessel such as a graft vessel. The relative separation of the compression plates is reduced to the extent necessary to bring the everted edges of the anastomosed structures into contact engagement so that a leak proof anastomosis is achieved.

A feature of the present invention is that the anvil is configured in a way such that it cooperates with the cutting element in the opening of the anastomosis fenestra in the target vessel and it also cooperates with the compression plate apparatus in the eversion of the edge of the target vessel at the anastomosed fenestra. By joining the everted contour of the target vessel at the anastomosis fenestra with the everted edge of the graft vessel, significant exposure to the blood flow of the cut portion of the anastomosed structures is avoided. Furthermore, the use of the anvil in a plurality of operations permits a considerable simplification of the anastomosis procedure. These operations include the abutting of the receiving blood vessel wall at the anastomosis site, the opening of the anastomosis fenestra in the receiving blood vessel, the eversion of the edge of the target vessel at the anastomosis fenestra, and the joining of the anastomosed structures.

An external anastomosis operator is also provided that controls the anastomosis procedure once the anvil pull extends out of the wall of the vessel and can be engaged. The external anastomosis operator enables the anastomosis procedure to be mechanized so that it is rapidly and reliably completed in a highly controlled manner.

By not requiring the interruption of blood flow in the receiving blood vessel, the active endoscopic or peripheral procedure of this invention advantageously reduces or even eliminates the risk of ischemia in organs that receive their main supply of blood through the receiving blood vessel. Furthermore, the exposure of the anastomosis area is reduced because no devices have to be introduced to temporarily interrupt blood flow. This feature advantageously enhances the minimally invasive character of the methods, systems, and apparatuses of this invention and the intervention time for the practice of the anastomosis.

Additional aspects and advantages of this invention will be apparent from the following detailed description of preferred embodiments thereof, which proceeds with reference to the accompanying drawings.

BRIEF DESCRIPTION OF THE DRAWINGS

FIG. 1A is a perspective view of a cutting apparatus inserting an anvil through an insertion opening into the lumen of a blood vessel.

FIG. 1B is a perspective view of a cutting apparatus distending the vessel and being readied to form an opening in the vessel.

FIG. 1C is a cross-sectional view of the anvil pull of the cutting apparatus shown in FIGS. 1A–1B pulling the anvil so that the engaging end of the anvil engages the cutter and forms an opening.

FIG. 1D is a magnified, cross-sectional view of the engaging end and the cutter forming an opening.

FIG. 7A is a perspective view of mechanically expandable anvil.

FIG. 7B is a cross-sectional view of the anvil shown in FIG. 8A.

FIG. 8A is a perspective view of a chemically expandable anvil.

FIG. 8B is a cross-sectional view of the anvil shown in FIG. 8A.

DETAILED DESCRIPTION OF PREFERRED EMBODIMENTS

Figure 2A:
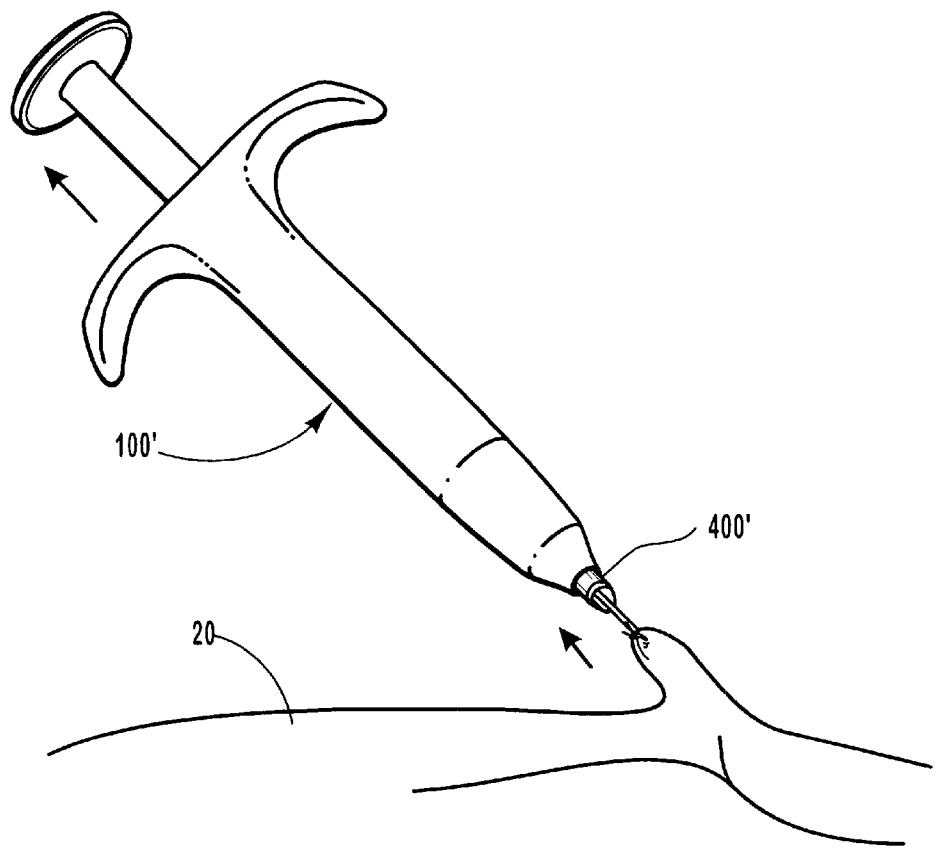
FIG. 2A is a perspective view of a cutting apparatus with an elliptical anvil.

The present invention relates to an externally positioned cutting apparatus that is inserted into a lumen through the wall of the lumen and then utilized for forming a vessel opening. The vessel opening is subsequently anastomosed to an opening in another vessel.

The apparatus of this invention accesses the anastomosis site through a small incision, such as an arteriotomy, made at the anastomosis site. The cutting apparatus of the present invention includes an anvil, an anvil pull and a cutter. The anvil is inserted into an anastomosis site through a small incision at the anastomosis site. The anvil is then inserted into the blood vessel and brought into contact with the interior wall of the vessel so that the anvil distends the wall of the vessel. The cutter is then urged against the portion of the vessel wall that is distended by the anvil to form an opening.

FIG. 1A is a perspective view of an externally positioned cutting apparatus 100 having an anvil 210 ready for insertion through an insertion opening 16 into the lumen of a blood vessel. FIG. 1B is a perspective view of cutting apparatus 100 distending vessel 20 and being readied for cutting.

As shown in FIG. 1C, a cross sectional view of a portion of cutting apparatus 100, cutting apparatus 100 has an anvil 210, an anvil pull 230, and a cutter 400. Anvil 210 and anvil pull 230 are preferably fixedly engaged together. The term "anvil" is meant to encompass objects with the characteristics described herein which present at least one surface that is adapted to engage a cutter. Anvil 210 is an example of an anvil means for engaging the interior surface of a first vessel at an anastomosis site. FIG. 1C shows the formation of an opening 25 as cylindrical cutting edge 414 engages spherical engaging end 212.

Cutter 400 includes a cutting tube 410 that terminates at a cutting knife 412 with a cutting edge 414. Cutter 400 may be made of any material sufficiently hard to form a vessel opening. In a preferred embodiment, cutter 400 is formed from stainless steel. A cutter of stainless steel is sufficiently hard to form a vessel opening and to puncture or inwardly depress engaging end 212 of anvil 210 made of a plastic material. Also, a cutter such as cutter 400, made from stainless steel, is sufficiently inexpensive to be a disposable, single use item. Cutter 400 is an example of a cutting means for forming a first vessel opening in the wall of the first vessel. Other examples of cutting means are discussed in U.S. patent application Ser. No. 09/736,781, referenced above. For example, a surgical laser may be used to open the anastomosis fenestra.

Cutter 400 of the apparatus of the present invention consistently creates a complete cut having a perimeter with a desired shape such as a circle or an ellipse depending on the type of anastomosis. The precision of the cutting is due to several features. The vessel wall is distended over the anvil which enables the wall to be stretched. This assists in creating a clean cut. Also, the anvil is preferably configured such that it has an engaging end that is convex and is more preferably spherical so that when engaged by a cylindrical cutter the cutter can self center on the engaging end. The cutter is also preferably spring biased which provides increased pressure for engaging the anvil.

Anvil 210 provides a surface at engaging end 212 for engaging cutter 400. Engaging end 212 is also in direct contact with the blood vessel's intima at the anastomosis site when anvil 210 abuts the receiving blood vessel wall. Anvil 210 is sized at engaging end 212 to have a greater cross-sectional area than a cross-sectional area defined by the perimeter of cutting edge 414 of cutter 400 such that portions of engaging end 212 extend beyond cutting edge 414 when cutter 400 engages anvil 210 and forms a first vessel opening 24. This size differential is particularly useful as it permits the anastomosis fenestra or vessel opening to be formed through the action of the cutting edge 414 pressing against engaging end 212. This is a significant improvement over conventional cutting techniques that involve the external positioning of an anvil into the lumen of a vessel that is smaller than the cutter so that the vessel is cut as the cutter passes over the anvil. More particularly, this configuration eliminates the possibility of a cut resulting in a "dangling chad" effect.

In addition, in the embodiment shown in FIG. 1D, anvil 210 is made of a material that can hold its shape under the pressure of cutter 400, but has a surface that is soft enough so that cutter 210 can puncture or penetrate into the surface of anvil 210. The softer material of the surface enables cutter 400 to puncture into anvil 210 when cutter 400 is urged against anvil 210. By cutting into anvil 210 while cutting vessel 20, the apparatus of the present invention consistently provides a clean cut and prevents threads of tissue or a "dangling chad" effect from remaining after cutting. Anvil 210 is preferably designed to be disposable. Anvil 210 may be made entirely of a material that is softer than cutter 400.

Figure 6A:
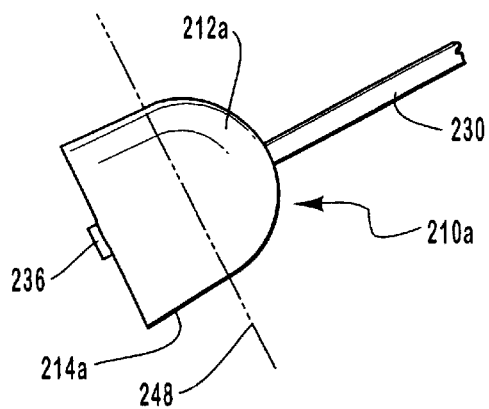
FIG. 6A is a perspective view of an alternative embodiment of an anvil having a slightly tapered landing.
Figure 6B:
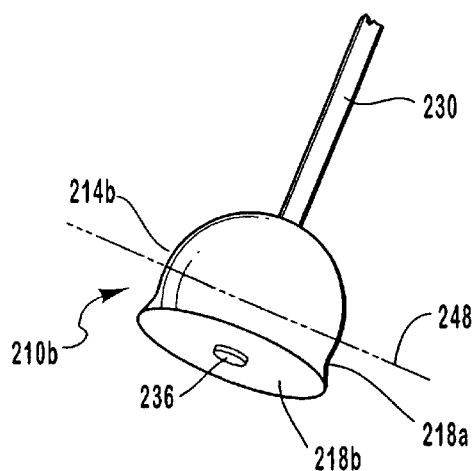
FIG. 6B is a perspective view of an alternative embodiment of an anvil having a flared flange.
Figure 6C:
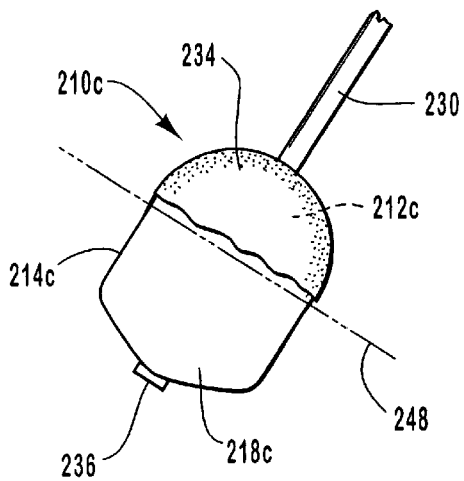
FIG. 6C is a perspective view of an alternative embodiment of an anvil having a tapered terminal end and a coated engaging end.

Alternatively, anvil 210 may have a soft material coating over a harder material as shown in FIG. 6C at 234.

Figure 5A:
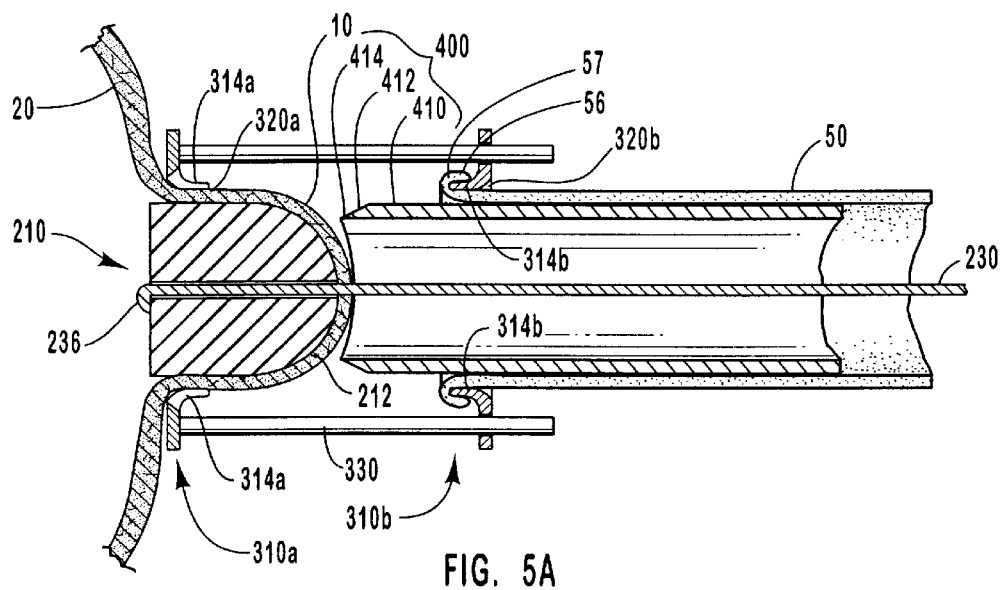
FIG. 5A is a cross-sectional view of the compression plate apparatus shown in FIG. 4C as an anvil distends a blood vessel into the compression plate apparatus.
Figure 5B:
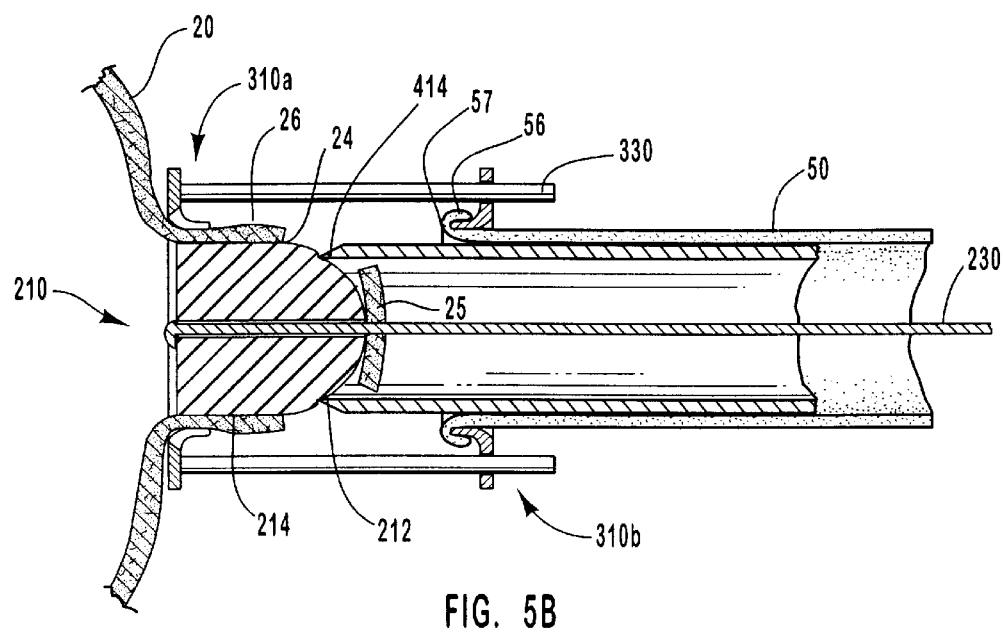
FIG. 5B is a cross-sectional view of the compression plate apparatus as shown in FIG. 5A in the next phase as a cutter and an anvil are engaged to form an opening in the vessel.

In one embodiment, anvil 210 is made of a material that is more flexible than cutter 400 and enables cutter 400 to depress the surface of anvil 210 inwardly when vessel 20 is cut, as shown in FIG. 5B. Anvil 210 may also be made of a material that is sufficiently resilient so that cutter 400 does not noticeably alter the surface of anvil 210. Of course anvil 210 may be formed from a material having about the same hardness as cutter 400. Additionally, anvil 210 and cutter 400 may be formed from the same material such as stainless steel.

Anvil 210 is preferably formed from a plastic material such as Delrin® acetal resins. Alternatively, anvil 210 may be formed from nylon, acrylic, Teflon®, polyvinylchloride, ultra high molecular weight polyethylene, high density polyurethane, polyester, polyethylene or any other biocompatible polymer. Anvil 210 may alternatively have a coating of Delrin® acetal resins or any of the other materials discussed as materials from which anvil 210 may be made. For example, in one embodiment, anvil 210 has a stainless steel core and a polyurethane coating.

Figure 5C:
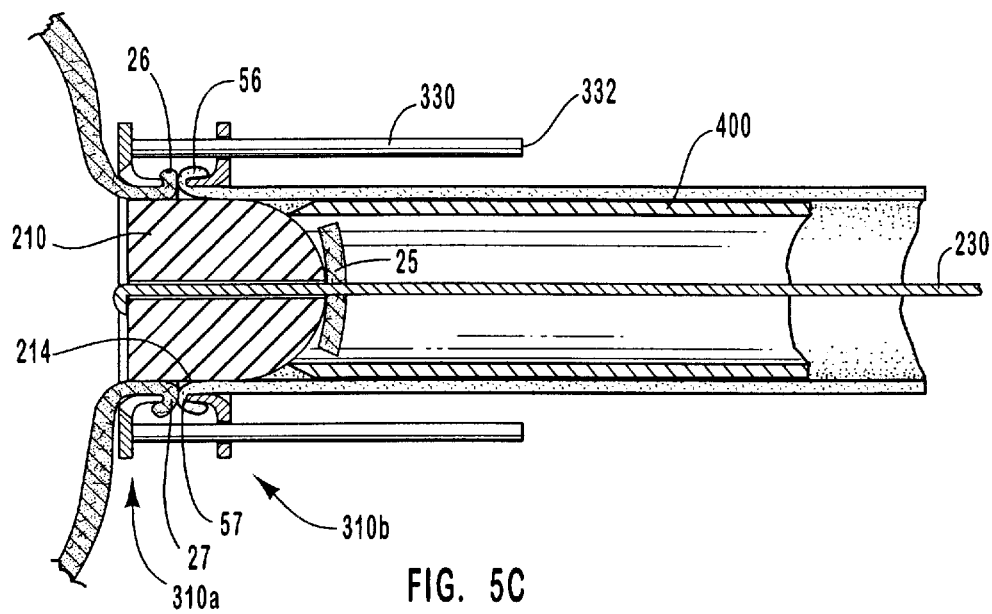
FIG. 5C is a cross-sectional view of the compression plate apparatus shown in FIG. 5B in the next phase after the second compression plate has been compressed towards the first compression plate such that the everted graft vessel contacts the everted blood vessel.
Figure 6D:
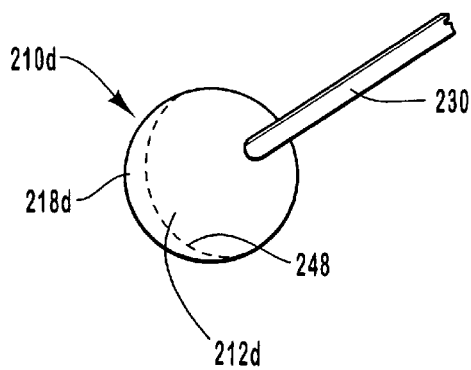
FIG. 6D is a perspective view of an alternative embodiment of a spherical anvil.
Figure 6E:
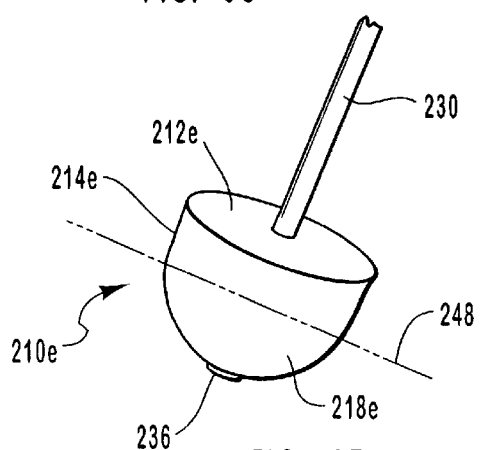
FIG. 6E is a perspective view of an alternative embodiment of an anvil having a flat engaging end.
Figure 6F:
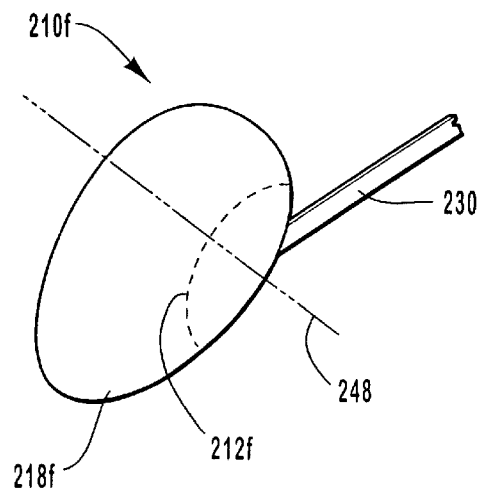
FIG. 6F is a perspective view of an anvil having an elliptical engaging end and an eccentrically connected anvil pull.

Anvil 210 and anvil pull 230 are preferably fixedly attached together. Anvil pull 230 extends through anvil 210 via an anvil aperture 216 (not shown) and terminates at a stopping element 236, as shown in FIG. 4D. Since the anvil pull is typically metal and the anvil is typically molded plastic, stopping element 236 may be just the proximal end of anvil pull 230 embedded in anvil 210 such that it is still visible as shown is FIGS. 5A–5C. Of course, the proximal end may be embedded in a way such that it is not visible as shown in FIGS. 6D and 6F. In the embodiment shown in FIG. 5A, the stopping element 236 is the proximal end of anvil pull 230 that has been bent so that it is partially embedded in terminal end 218 of anvil 210. Anvil 210 and anvil pull 230 may also be integral as shown in FIGS. 1C and 2B. Additionally, anvil 210 may be movably positioned on anvil pull 230 in which case, stopping element 23 can be used to brace against terminal end 218 of anvil 210. Further, a portion of the anvil may be movably positioned on the anvil pull as shown in FIGS. 7A–7B.

Figure 2B:
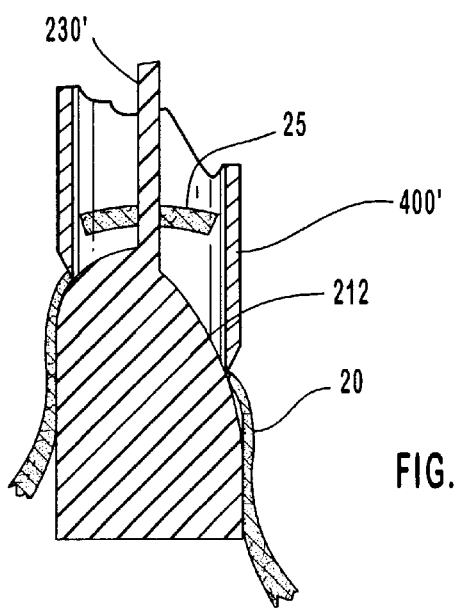
FIG. 2B is a cross-sectional view and the anvil pull of the cutting apparatus shown in FIGS. 2A pulling the anvil so that the engaging end of the anvil engages the cutter and forms an elliptical opening.

Note that, as shown by FIGS. 2A–2B, externally positioned anvils may be used to form noncircular openings. These anvils have an engaging end with a shape corresponding to that of the cutting edge of a cutter such that the first vessel opening is formed as the noncircular cutting edge presses against the engaging end. FIG. 6F also shows such a convex, elliptical cutting edge as discussed below.

Figures 3A, 3B:
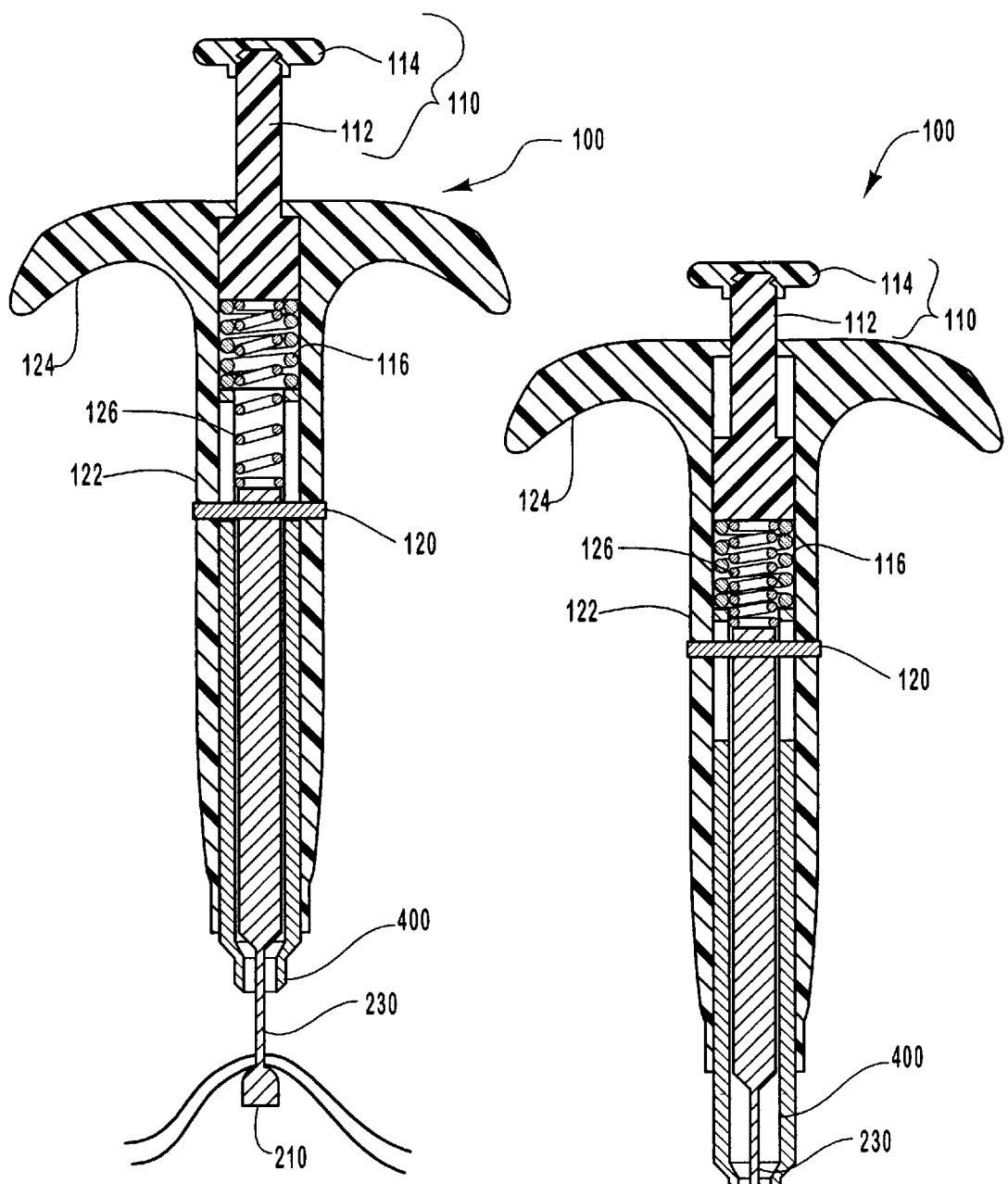
FIG. 3A is a cross-sectional view of a spring biased cutting apparatus after the anvil has been inserted through an insertion opening.
FIG. 3B is a cross-sectional view of the spring cutting apparatus shown in FIG. 3A as the anvil pull is pulled against the cutter.

FIGS. 3A–3B provide cross-sectional views of cutting apparatus 100 which reveal that it is spring biased. Spring biased cutting apparatus 100 has a handle 110 that includes a stem 112 and a handle cap 114. Apparatus 100 also has a casing 122 and grasping handle 124. Stem 112 travels within a chamber as shown by comparing FIGS. 3A–3B to push against a high tension spring 116 that pushes against a cutter 400. While cutter 400 is movable, anvil pull 230 moves a greater distance in order to contact cutter 400.

A pin 120, shown in FIGS. 1A and 1B, extends through anvil pull 230 and casing 122 such that movement of grasping handle 124, which is an integral component of casing 122, also moves anvil pull 230. Pin 120 travels within a groove 118 as shown in phantom lines in FIGS. 1A–1B. As depicted in FIGS. 3A and 3B, the distal end of anvil pull 230 abuts a low tension spring 126 concentrically positioned within high tension spring 116. When handle cap 114 is depressed and grasping handle 124 is lifted towards handle cap 114, anvil pull 230 and anvil 210 are drawn up with handle 124, casing 122 and pin 120. Cutter 400 is simultaneously pressed towards anvil 210 by the downward movement of spring 116 as handle cap 114 is depressed.

Once cutter 400 is brought into contact with anvil 210, the spring biasing of cutter 400 enables cutter 400 to be pushed back by anvil 210, allowing anvil 210 to further distend the wall of vessel 20 as shown in FIGS. 3A–3B. As anvil 210 pushes cutter 400 through vessel 20, anvil 210 causes cutter 400 to retract, however, increasing resistance is encountered as spring 116 becomes further compressed. Spring 116 is an example of a spring biasing means for providing tension against the cutting means.

As cutter 400 applies increasing amounts of pressure to vessel 20 anvil 210 continues to stretch the wall of vessel 20 into compression plate apparatus 300. By optimizing features such as the tension of the spring and the length of cutter, vessel 20 is distended far enough into compression plate apparatus 300 to leave sufficient lengths of the vessel in the compression plate apparatus for capturing in the subsequent eversion process. It has been found that about 17–18 lbs or about 20 lbs is ideal for forming the anastomosis fenestra.

The gradual increase in pressure also serves to assist a spherical engaging end 212 of anvil 210 to self center on cutter 400. Since the pressure increases gradually, if anvil 210 is initially misaligned on cutter 400 then the gradual increase in pressure causes the anvil to be gradually drawn to center as the spherical engaging end 212 is pulled into a chamber or recess of the cutting device. If pressure is applied too rapidly, the sharp cutting edge 414 of a cutter such as cutter 400 may dig into anvil 210 before anvil 210 can slide into a centered orientation. Accordingly, the use of a cutter with at least a recess at its cutting end and a spherical engaging end accommodates imperfections in the alignment of the cutter and the anvil.

Figure 4A:
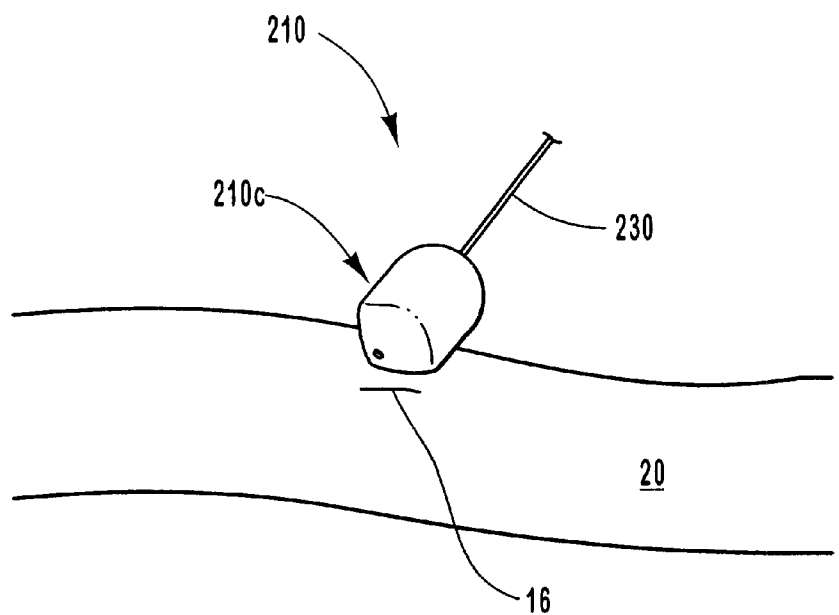
FIG. 4A is a perspective view of an anvil being inserted from the exterior of a blood vessel into the blood vessel lumen.
Figure 4B:
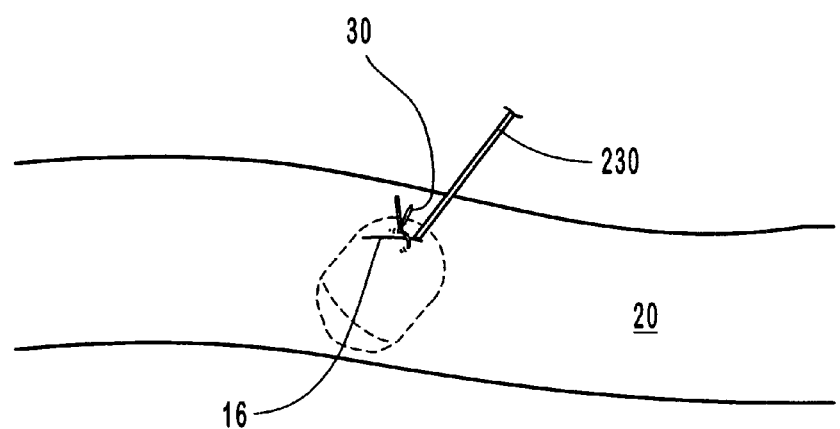
FIG. 4B is a perspective view of the blood vessel shown in FIG. 4A with the anvil depicted in phantom lines and a stay suture around the insertion opening.
Figure 4C:
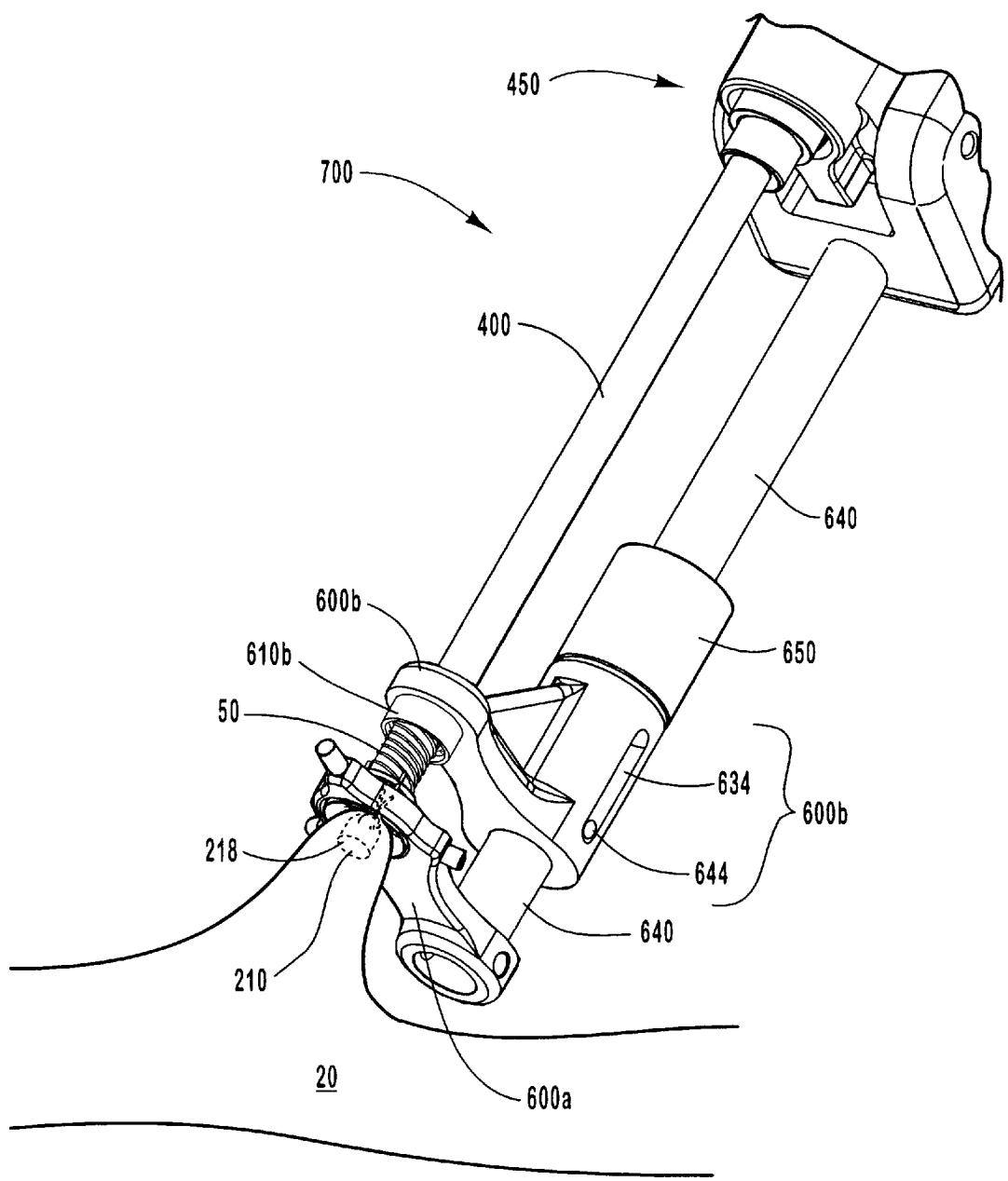
FIG. 4C is a perspective view of an external anastomosis operator cooperating with the anvil depicted in phantom lines to form an anastomosis.
Figure 4D:
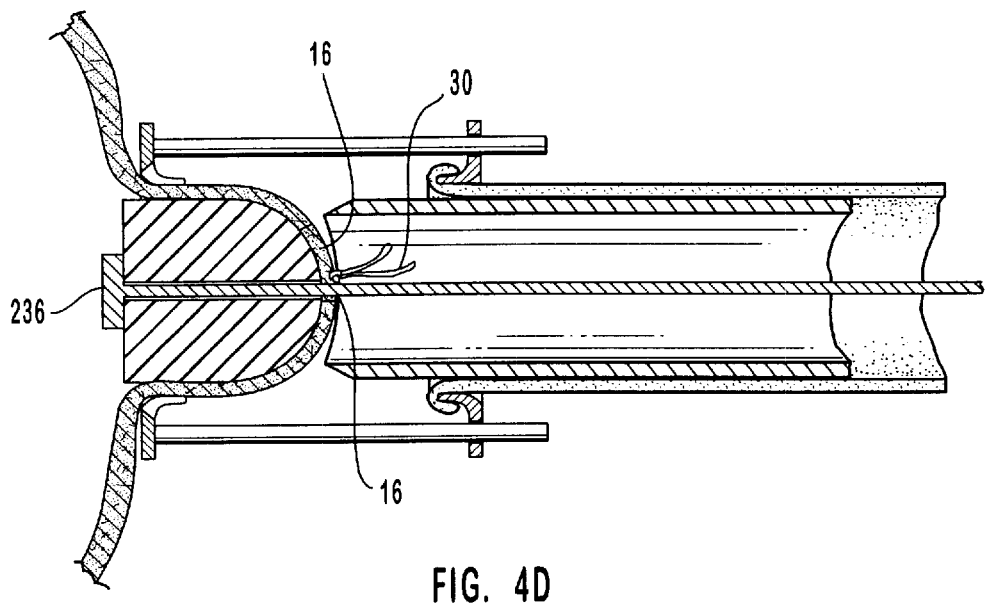
FIG. 4D is a cross-sectional view of a compression plate apparatus as the anvil distends a blood vessel having a stay suture around the insertion opening.

FIGS. 4A–4E depict the primary steps involved in creating an anastomosis through the use of a cutting apparatus of the present invention in combination with an external anastomosis operator. FIG. 4A depicts an insertion opening 16 that has been made in vessel 20. Insertion opening 16 is preferably just large enough to permit an anvil such as anvil 210a as shown in FIG. 6A or any of the other anvils disclosed herein to be externally positioned into the lumen of vessel 20. After anvil 210a has been inserted though a wall of first vessel 20 at insertion opening 16 that has been selected as an anastomosis site such that anvil pull 230 extends through insertion opening 16, then a stay suture 30 or several stay sutures may alternatively be used to partially close insertion opening 16.

An anvil that has a tapered terminal end 218 such as terminal end 218c of anvil 210c or terminal end 219d of anvil 210d may be more easily inserted. Note that FIGS. 4C–4E, however, show an anvil 210 that has been inserted from outside of vessel 20 that has a nontapered terminal end 218. As shown in FIG. 4C, anvil pull 230 is loaded into an external anastomosis operator 700 for the anastomosis procedure.

FIG. 4D depicts anvil pull 230 extending through a compression plate apparatus 300 and into chamber 420 of cutter 400 such that cutting edge 414 self centers and seats on spherical engaging end 212 of anvil 210. Stay suture 30 enables anvil 210 to distend the wall of vessel 20 since stay suture 30 reduces the size of insertion opening 16. Compression plate apparatus 300 has a first compression plate 310a with a first compression plate opening 320a and a second compression plate 310b with a compression plate opening 320b. Compression plate openings 320a and 320b are sized to permit the anvil pass through openings 320a, 320b with a portion of the first vessel, as shown in FIGS. 5C.

Figure 4E:
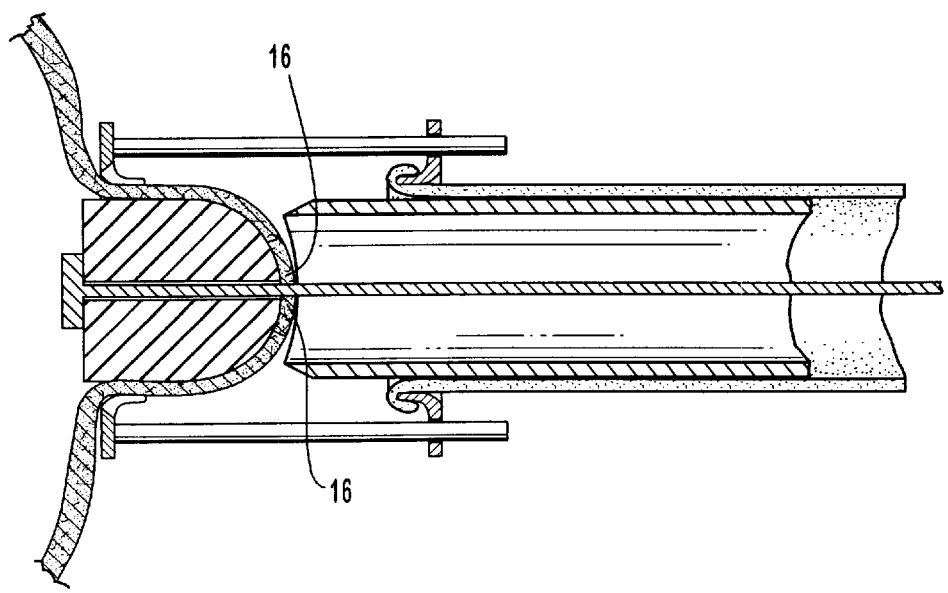
FIG. 4E is a cross-sectional view of the compression plate apparatus shown in FIG. 4D as an anvil distends a blood vessel after being inserted into the lumen of the blood vessel through an insertion opening.

FIG. 4E shows that it is possible to complete the same step shown in FIG. 4D without a stay suture 30 as long as the distension of the wall of vessel 20 does not cause insertion opening 16 to increase in size such that it becomes so large that a part of it is beyond the reach of cutting edge 414 of cutter 400. Another method for enabling the wall of the vessel to be distended for the subsequent eversion process to occur in the desired manner involves the minimization of the size of insertion opening 16 through the use of expandable anvils. As discussed below, anvils may be utilized that are expanded or deployed at the anastomosis site.

FIGS. 5A–5D depict the use of a compression plate apparatus 300 in combination with a cutter 400 and anvil 210 in the sequential order according to the preferred methodology. To optimally present this sequence, FIGS. 5A–5D are cross-sectional views. FIG. 5A depicts anvil 210 being pulled against the intima or interior of the vessel wall such that vessel 20 is sufficiently distended to permit the vessel 20 at anastomosis site 10 to be pulled into compression plate apparatus 300 through first compression plate opening 320a. More particularly, anvil 210 is pulled by anvil pull 230 such that all of spherical engaging end 212 is pulled into the compression plate apparatus 300 and most of cylindrical landing 214. Cutter 400 also is shown in FIG. 5A extending through second compression plate opening 320b about half way through compression plate apparatus 300 as cutter 400 is approximated with the portion of the blood vessel 20 distended by anvil 210. Compression plate apparatus 300 is an example of a means for joining a portion of the first vessel that defines the first vessel opening to a portion of a second vessel that defines a second vessel opening.

FIG. 5B depicts the formation of a first vessel opening 24 in the wall of the first vessel. First vessel opening 24 is formed by pulling anvil pull 230 through cutter 400 sufficiently to enable anvil 210 to advance blood vessel 20 against cutting edge 414. After the cut has been made then a cut portion 25 of the wall of blood vessel 20 remains on spherical engaging end 212 of anvil 210 while the portion 26 of the blood vessel that now define first vessel opening 24 rest on anvil landing 214. Landing 214 aids in everting the tissue that is to be anastomosed. Cutter 400 is preferably spring biased.

Figure 5D:
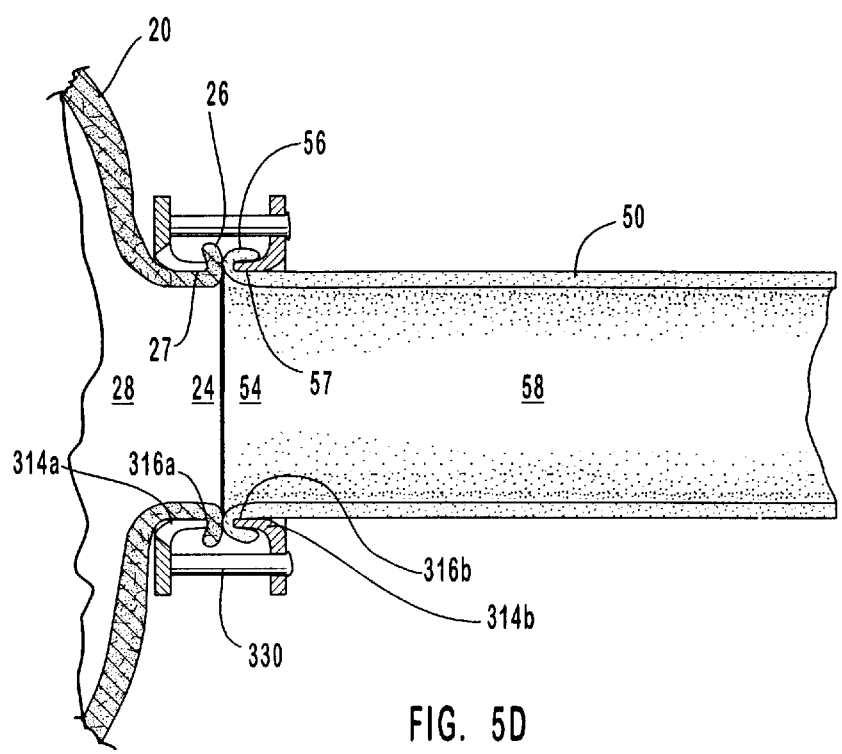
FIG. 5D is a cross-sectional view of the compression plate apparatus shown in FIG. 5C with the anastomosed structure after the anvil apparatus and the cutter have been removed.

FIG. 5C depicts compression plate apparatus 300 after compression. Note that the everted portion 56 of graft vessel 50, more particularly the portion 57 opposite from the rounded tip 316b, is urged against portion 26 that defines first blood vessel opening 24 in a manner such that portion 26 has been everted. The end result is that the portion 27 opposite from rounded tip 316a is held in contact with the portion 57 of vessel 50 opposite from distal rounded tip 316b. As shown in FIG. 5D, after compression plate apparatus 300 has been compressed to join portion 26 of blood vessel 20 that defines first vessel opening 24 to portion 56 of second vessel 50 that defines graft vessel opening 54 then first vessel 20 and second vessel 50 are anastomosed together and are in fluid communication. Anvil apparatus 200 and cutter 400 have been removed upon the completion of the procedure through lumen 58 of graft vessel 50. More particularly, once the anastomosis is completed then anvil pull 230 is pulled so that it draws anvil 210 through openings 320a and 320b of compression plate apparatus 300 such that anvil apparatus 200 is removed along with cutter 400 through lumen 58.

FIGS. 6A–6F provide examples of several embodiments of the anvil of this invention. A line 248 is a visual aid drawn through anvils 210a–d is provided to clearly indicate that the portion of the anvil extending from line 248 to the anvil pull is the engaging end 212a–d.

Engaging end 212 can have any shape suitable for engaging the interior wall of first vessel. Engaging 212 may be convex and spherical or elliptical or may have any other similarly convex and curved surface suitable for engaging the cutter. As shown in FIGS. 6A–6D, engaging ends 212a–d are all convex and spherical. Note that these spherical engaging ends are essentially a hemisphere at the side of the anvil proximal to the anvil pull 230. This spherical shape enables anvil 210 to distend the vessel wall to provide for a clean, complete cut. The shape also enables the cutting device to center on anvil 210, providing a cut of the desired shape. When the cutting device is cylindrical and is configured such that it permits part of the spherical engaging end of the anvil to be positioned in the chamber 420, then the cutter self centers on a spherical engaging end. Alternatively, as depicted in FIG. 6E, anvil 210e has an engaging end that is a flat surface. In addition to flat engaging ends, another example of an engaging end that is not curved is an engaging end that is conical.

As mentioned above, FIG. 6F depicts an anvil 210d having an elliptical engaging end that is adapted to receive a cutter with a corresponding elliptical configuration for the formation of elliptical openings in vessels. It is often necessary to attach vessels in a nonperpendicular configuration such that it is Y-shaped instead of T-shaped. While reference is made to spherical engaging ends it should be noted that noncircular engaging ends that are convex and curved such as the elliptical engaging end of anvil 210d may also be utilized to achieve the desired eversion, particularly when the anvil has an appropriately configured landing.

As depicted in FIGS. 6A–6F, anvil 210 has a terminal end 218. Terminal end 218 may be a flat surface as shown in FIGS. 6A and 6B. FIG. 6C depicts an alternative embodiment, an anvil 210c that has a tapered terminal end 218c. FIGS. 6D and 6E depict spherical convex terminal ends 218d–e. As shown in FIG. 6F, terminal end 210f has a convex, elliptical terminal end 218f. As discussed above in reference to FIGS. 1A–1C, FIGS. 2A–2B, FIGS. 3A–3B, and FIGS. 4A–4E, an anvil 210 is inserted though a wall of a blood vessel at an insertion opening that has been selected as an anastomosis site. Anvil 210 is then positioned in a lumen of the first vessel with the anvil pull 230 extending through the insertion opening of the blood vessel. When anvils such as anvils 210a–b are inserted, it may be necessary to stretch the vessel walls. Use of an anvil with a tapered, spherical or elliptical terminal end such as terminal ends 218c–f may minimize the size needed for the insertion opening since the vessel wall can gradually stretch as the taper of the terminal end 218c increases.

Anvil 210 preferably includes a landing 214. In the embodiments shown in FIGS. 6A and 6B, landing 214 is a cylindrical surface. As discussed above, after a cut has been made a cut portion 25 of the wall of blood vessel 20 remains on spherical engaging end 212 of anvil 210 while the portion 26 of the blood vessel that now defines first vessel opening 24 rests on anvil landing 214. By providing a surface against which first vessel opening 24 rests, landing 214 aids in everting the tissue that is to be anastomosed.

FIGS. 7A–7B and FIGS. 8A–8B each depict an anvil apparatus with an anvil that is deployable after reaching the anastomosis site such that they have an expanded size when needed. FIGS. 7A–7B depict a mechanically deployable anvil while FIGS. 8A–8B depict a chemically deployable anvil.

FIGS. 7A–7B depict a flexible anvil 210" that is narrow when collapsed and becomes wider when its engaging end 212" encounters the wall of blood vessel 20. The engaging end 212" of anvil 210" is not attached to anvil pull 230, only terminal end 218" is attached to anvil pull. Since anvil 210" is hollow, it can flex into an expanded or deployed position when engaging end 212" is pushed toward terminal end 218".

FIG. 8A depicts a balloon anvil 210''' in a deflated condition extending from a hollow tubular anvil pull 230". FIG. 8B depicts balloon anvil 210''' deployed in an inflated condition ready for engagement against the interior of a vessel at an anastomosis site. Balloon anvil 210" is preferably chemically deployed by being filled with a polymerizable material that hardens in situ. For example, syringe 280 may be coupled to tubular anvil pull 230 to enable a composition to be delivered that includes conventional monomers that rapidly polymerizes in the presence of appropriate chemical initiators.

For example, the monomers may be suitable acrylates such as urethane dimethacrylate, p-hydroxyphenyl methacrylamide, butane diol dimethacrylate, and bisphenol-A-diglycidyl dimethacrylate ("Bis-GMA"). Examples of appropriate chemical initiators include a wide range of peroxides, other per components, and other free radical generators. An appropriate two-part chemical curing system typically includes a peroxide constituent in one part and an amino compound in another. Exemplary peroxides include benzoyl peroxide, 2-butanone peroxide, lauroyl peroxide and tert-butyl peroxide. Examples of amino compounds include dimethylamino ethyl methacrylate, triethyl amine, 2-dimethylamino ethanol, diethylamino ethyl methacrylate, trihexyl amine, N,N-dimethyl-p-toluidine, N-methylethanolamine, and 2,2'(p-tolyimino) diethanol.

After the polymerizable material, the mixture of monomers and chemical initiators, has been delivered into balloon anvil 210''' then it is necessary to wait for the material to polymerize such that anvil 210''' is hard. As shown in FIG. 8B, once the polymerizable material has hardened then anvil pull 230" is anchored in polymerized material 222 and polymerized material 222 is surrounded by balloon 220. Since anvil pull 230" is anchored in polymerizable material 222, balloon anvil 210 can be used in a cutting process without regard to the softness of balloon 220. More particularly, if a cutter 400 presses through balloon 220 then it merely rests on the exposed polymerized material 222 with the cut portion of blood vessel 20 and is removed along with the entire anvil apparatus 200''' The balloon anvil may also be treated with an appropriate material such that it is puncture resistant.

Additionally, the balloon may be a puncture resistant, but flexible, balloon. Puncture and scratch resistant balloons have been disclosed in U.S. Pat. Nos. 5,766,158, 5,662,580, 5,620,649, 5,616,114, 5,613,979, 5,478,320, 5,290,306, and 5,779,731, which are hereby incorporated by reference in their entirety. In still another embodiment of this invention, the anvil of this invention can be embodied by the combination of a balloon and a puncture resistant balloon sheath. A balloon plus balloon sheath combination has been disclosed in U.S. Pat. No. 5,843,027 which is hereby incorporated by reference in its entirety.

Figures 9A, 9B:
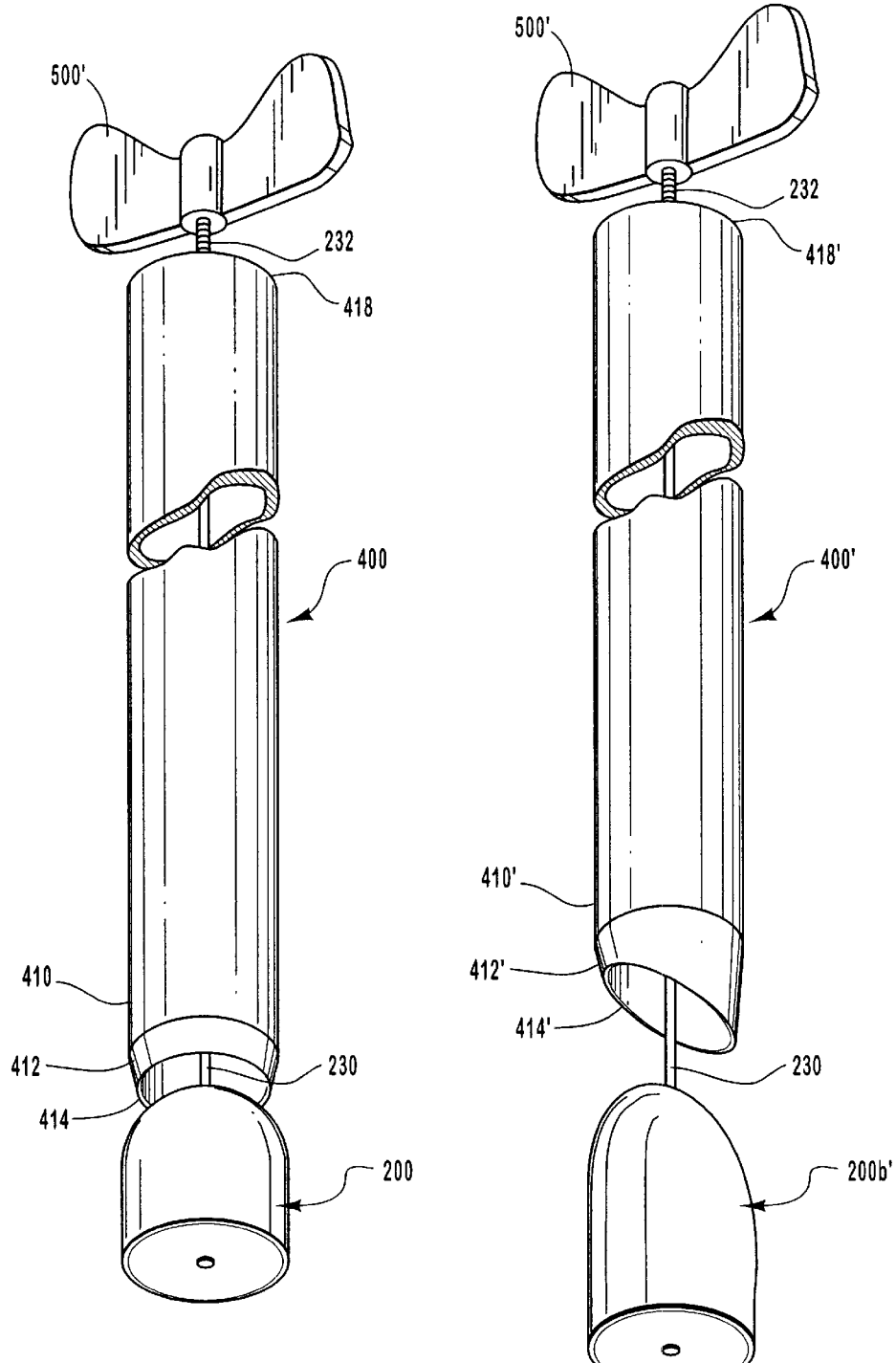
FIG. 9A is a perspective view of a cutter ready to engage an anvil with a thread anvil pull extending through the cutter to an anvil pull engager to form a circular opening.
FIG. 9B is a perspective view of a cutter ready to engage an anvil with a thread anvil pull extending through the cutter to an anvil pull engager to form an elliptical opening.

FIGS. 9A–9B depict a simple combination of a cutter engaging an anvil as the anvil pull 230''' is advanced by an anvil pull engager 500' which holds and advances anvil pull 230'''. Note that distal end 232 of anvil pull 230 is threaded and anvil pull engager is essentially a wingnut that is correspondingly threaded. As anvil pull engager 500' tightens against the distal end 418 of cutter 400 then anvil pull 230 pulls anvil 200 until cutter 400 is engaged. Of course, an even simpler design is the manual application of pressure by pulling on anvil pull while pushing on cutter without an anvil pull engager.

The dimensions of any of the embodiments of the anvil of this invention are determined by the size of the lumen of the receiving vessel and by the dimension of the passage that will ensure the fluid communication between the graft vessel and the receiving vessel after they have been anastomosed. These dimensions are typically chosen or known in the art. For example, when a graft vessel of about 4 mm in diameter is to be anastomosed to a receiving blood vessel which has an approximate lumen diameter of about 8 mm, the diameter of the anvil at its widest may range from about 3 mm to about 6 mm. So for anvil 210, the diameter at landing 214 may range from about 3 mm to about 6 mm for use in such a vessel. However, the anvil may have any suitable size that enables it to be positioned as needed. Note that the anvil is preferably designed so that the blood flow through the receiving blood vessel will preferably not be interrupted during the anastomosis. However, the design can be such that the blood flow is interrupted when this feature is desired.

In summary, the anvil is configured in such a way to effectively cooperate with the cutter to form the opening of the anastomosis fenestra. The anvil also preferably cooperates in the eversion of the edge of the anastomosed fenestra. Furthermore, the anvil of the present invention is configured so that it can abut the receiving blood vessel wall at the anastomosis site from the intraluminal space of such blood vessel. In addition, the anvil of this invention is configured so that it effectively cooperates with the compression plate apparatus in the joining of the anastomosed structures. It will be obvious to those having skill in the art that many changes may be made to the details of the above-described embodiments of this invention without departing from the underlying principles thereof. The scope of the present invention should, therefore, be determined only by the following claims.

What is claimed is:

1. An anastomosis system comprising:
   an externally positioned anvil apparatus including anvil means for engaging an interior surface of a wall of a first vessel at an anastomosis site, and anvil pull means for holding an engaging end of the anvil means against the interior surface of the wall of the first vessel, the anvil pull means extending from the engaging end of the anvil means, wherein the engaging end is convex; and
   an external anastomosis operator including
   engaging means for engaging the anvil pull means once the anvil means has been inserted though the wall of the first vessel at an insertion opening that has been selected as an anastomosis site and positioned in a lumen of the first vessel with the anvil pull means extending through the insertion opening of the first vessel to enable the engaging means to hold the anvil pull means;
   cutting means for forming a first vessel opening in the wall of the first vessel at the anastomosis site through engagement with the anvil means of the anvil apparatus as the engaging means holds the anvil pull means after receiving the anvil pull means through the cutting means, the cutting means having a cutting perimeter that defines the shape of the first vessel opening;
> wherein the engaging end of the anvil means has a greater cross-sectional area than a cross-sectional area defined by the cutting perimeter of the cutting means such that portions of the engaging end of the anvil means extend beyond the cutting perimeter when the cutting means engages the anvil means and forms the first vessel opening, and wherein the engaging end of the anvil means is adapted to engage an area of the interior surface of the wall of the first vessel which is greater than the cross-sectional area defined by the cutting means.

2. An anastomosis systems as claimed in claim 1 wherein the engaging end of the anvil means is a spherical engaging end, and wherein the cutting means includes a cutting tube that terminates at cutting knife with a circular cutting edge such that the first vessel opening is formed as the circular cutting edge presses against the spherical engaging end.

3. An anastomosis system as claimed in claim 1, wherein the cutting means includes a cutting tube that terminates at cutting knife with a noncircular cutting edge and wherein the engaging end of the anvil means has a shape corresponding to that of the cutting edge such that the first vessel opening is formed as the noncircular cutting edge presses against the engaging end.

4. An anastomosis system as claimed in claim 1, wherein the anvil means is an expandable anvil having an initial collapsed position for insertion into the insertion opening and an expanded position, wherein the engaging end has a greater cross-sectional area than the cross-sectional area defined by cutting perimeter of the cutting means when in the expanded position.

5. An anastomosis system as claimed in claim 4, wherein the expandable anvil is mechanically deployable.

6. An anastomosis system as claimed in claim 4, wherein the expandable anvil is chemically deployable.

7. An anastomosis system as claimed in claim 1, wherein the anvil means is rigid.

8. An anastomosis system as claimed in claim 1, wherein the anvil means is solid.

9. An anastomosis system as claimed in claim 1, further comprising spring biasing means for providing tension against the cutting means as the cutting means engages the anvil means of the intraluminally directed anvil apparatus.

10. An anastomosis system as claimed in claim 9, wherein the spring biasing means provides an amount of tension that enables the cutting means to form the first vessel opening after the wall of the first vessel has been distended by the action of the anvil means being pulled into the openings of a compression plate apparatus such that forming the first vessel opening results in at least partial eversion of the portion of the first vessel defining the first vessel opening.

11. An anastomosis system as claimed in claim 1, further comprising means for joining a portion of the first vessel that defines the first vessel opening to a portion of a second vessel that defines a second vessel opening.

12. An anastomosis system as claimed in claim 1, further comprising a compression plate apparatus including a first compression plate having a first compression plate opening configured for alignment with the first vessel opening and a second compression plate having a second compression plate opening configured for alignment with a second vessel opening of a second vessel, the openings being sized to permit the anvil means to pass through the openings and out of the compression plate apparatus after the compression plates have been brought together to enable a portion of the first vessel defining the first vessel opening and a portion of the second vessel defining the second vessel opening to be joined such that the first vessel and the second vessel are anastomosed together.

13. An anastomosis system comprising:
an externally positioned anvil apparatus including an anvil pull extending from an engaging end of an anvil, wherein the engaging end is convex; and
an external anastomosis operator including
> an anvil pull engager adapted to hold the anvil pull extending from the anvil of the externally positioned anvil apparatus once the anvil has been inserted though a wall of the first vessel at an insertion opening that has been selected as an anastomosis site and positioned in a lumen of the first vessel with the anvil pull extending through the insertion opening of the first vessel; and
> a cutting device that is adapted to engage the anvil of the externally positioned anvil apparatus once the engager has received the anvil pull through the cutting device in order to form an opening in the wall of the first vessel at the anastomosis site, wherein the engager and the cutting device are adapted to enable the anvil pull to be moved through the cutting device, the cutting device including a cutting tube that terminates at a cutting knife with a cutting edge that defines the shape of the first vessel opening such that the first vessel opening has a perimeter that corresponds with the perimeter of the cutting edge,
>> wherein the cross-sectional area defined by the perimeter of the cutting edge of the cutting knife is smaller than a cross-sectional area of the engaging end such that portions of the engaging end of the anvil extend beyond the cutting edge when the cutting device engages the anvil and forms the first vessel opening, and
>> wherein the cross-sectional area of the engaging end of the anvil combined with the shape of the engaging end enables the cutting edge to cut against the engaging end at any position in which the cutting edge is initially set against the engaging end.

14. A cutting apparatus comprising:
anvil means for engaging an interior surface of a wall of a first vessel at an anastomosis site, and anvil pull means for holding an engaging end of the anvil means against the interior surface of the wall of the first vessel, the anvil pull means extending from an engaging end of the anvil means; and
cutting means for forming a first vessel opening in the wall of the first vessel at the anastomosis site through engagement with the anvil means;
> wherein the cutting means includes a cutting tube that terminates at a cutting knife with a cutting edge that defines the shape of the first vessel opening,
> wherein the anvil pull means extends within the cutting tube to enable the anvil pull means and the cutting means to be moved relative to each other,
> wherein the engaging end has a surface with a convex configuration, and
> wherein the cross-sectional area defined by the perimeter of the cutting edge of the cutting knife is smaller than a cross-sectional area of the engaging end such that portions of the engaging end of the anvil means extend beyond the cutting edge when the cutting means engages the anvil means and forms the first vessel opening.

15. A cutting apparatus as claimed in claim 14, wherein the engaging end of the anvil means is a spherical engaging end, and wherein the cutting edge is circular such that the first vessel opening is formed as the circular cutting edge presses against the spherical engaging end.

16. A cutting apparatus as claimed in claim 14, wherein the cutting edge is noncircular and wherein the convex shape of the engaging end of the anvil means corresponds to that of the cutting edge such that the first vessel opening is formed as the noncircular cutting edge presses against the engaging end.

17. A cutting apparatus as claimed in claim 14, wherein the anvil means is an expandable anvil having an initial collapsed position for insertion into the first vessel and an expanded position, wherein the engaging end has a greater cross-sectional area when in the expanded position than the cross-sectional area defined by cutting perimeter of the cutting means.

18. A cutting apparatus as claimed in claim 17, wherein the expandable anvil is mechanically deployable.

19. A cutting apparatus as claimed in claim 17, wherein the expandable anvil is chemically deployable.

20. A cutting apparatus as claimed in claim 14, wherein the anvil means is rigid.

21. A cutting apparatus as claimed in claim 14, wherein the anvil means is solid.

22. A cutting apparatus comprising:
  an anvil adapted to engage the interior surface of a first vessel at an anastomosis site, and an anvil pull extending from an engaging end of the anvil that is adapted to hold the engaging end of the anvil against the interior of the first vessel;
  a cutting device that is adapted to engage the anvil and form a first vessel opening in the wall of the first vessel at the anastomosis site, the cutting device including a cutting tube that terminates at a cutting knife with a cutting edge that defines the shape of the first vessel opening,
    wherein the anvil pull extends within the cutting tube to enable the anvil pull and the cutting device to be moved relative to each other,
    wherein the engaging end has a surface with a convex configuration, and
    wherein the cross-sectional area defined by the perimeter of the cutting edge of the cutting knife is smaller than a cross-sectional area of the engaging end such that portions of the engaging end of the anvil extend beyond the cutting edge when the cutting device engages the anvil and forms the first vessel opening.

23. A cutting apparatus as claimed in claim 22, wherein the engaging end of the anvil is spherical, and wherein the cutting edge is circular such that the first vessel opening is formed as the circular cutting edge presses against the spherical engaging end.

24. A cutting apparatus as claimed in claim 22, wherein the cutting edge is noncircular and wherein the convex shape of the engaging end of the anvil corresponds to that of the cutting edge such that the first vessel opening is formed as the noncircular cutting edge presses against the engaging end.

25. A cutting apparatus as claimed in claim 22, wherein the anvil is an expandable anvil such that the anvil has an initial collapsed position for insertion into the first vessel and an expanded position, wherein the engaging end has a greater cross-sectional area when in the expanded position than the cross-sectional area defined by cutting edge.

26. A cutting apparatus as claimed in claim 25, wherein the expandable anvil is mechanically deployable.

27. A cutting apparatus as claimed in claim 25, wherein the expandable anvil is chemically deployable.

28. A cutting apparatus as claimed in claim 22, wherein the anvil is rigid.

29. A cutting apparatus as claimed in claim 22, wherein the anvil is solid.

30. A cutting apparatus comprising:
  a rigid anvil adapted to engage the interior surface of a first vessel at an anastomosis site, and an anvil pull extending from an engaging end of the anvil that is adapted to hold the engaging end of the anvil against the interior of the first vessel;
  a cutting device that is adapted to engage the anvil and form a first vessel opening in the wall of the first vessel at the anastomosis site, the cutting device including a cutting tube that terminates at a cutting knife with a cutting edge that defines the shape of the first vessel opening,
    wherein the anvil pull extends within the cutting tube to enable the anvil pull and the cutting device to be moved relative to each other,
    wherein the engaging end has a surface with a convex configuration,
    wherein the cross-sectional area defined by the perimeter of the cutting edge of the cutting knife is smaller than a cross-sectional area of the engaging end such that portions of the engaging end of the anvil extend beyond the cutting edge when the cutting device engages the anvil and forms the first vessel opening.

* * * * *

UNITED STATES PATENT AND TRADEMARK OFFICE
CERTIFICATE OF CORRECTION

| | |
|---|---|
| PATENT NO. | : 6,626,921 B2 |
| APPLICATION NO. | : 10/003956 |
| DATED | : September 30, 2003 |
| INVENTOR(S) | : Blatter et al. |

It is certified that error appears in the above-identified patent and that said Letters Patent is hereby corrected as shown below:

Item [73] the name of the Assignee should be "Vital Access Corporation, Salt Lake City, UT (US)" pursuant to a Merger Agreement recorded on February 7, 2008, at Reel 020468, Frame 0721

Item [54] change title to --EXTERNALLY POSITIONED ANVIL APPARATUS FOR CUTTING ANASTOMOSIS FENESTRA--

Add the following prior art reference entered by the Examiner on February 4, 2003:

Journal of Thoracic and Cardiovascular Surgery Vol. 61, No. 5, May 1971, pages 705-709.

Add the following prior art references entered by the Examiner on July 21, 2003:

U.S. PATENT DOCUMENTS

| | | | |
|---|---|---|---|
| 6,007,576 | 12/1999 | McClellan | 623/1 |
| 5,951,576 | 09/1999 | Wakabayashi | 606/151 |
| 5,868,763 | 02/1999 | Spence et al. | 606/153 |
| 5,861,005 | 01/1999 | Kontos | 606/219 |
| 5,860,992 | 01/1999 | Daniel et al. | 606/145 |
| 5,843,027 | 12/1998 | Stone et al. | 604/53 |
| 5,843,088 | 12/1998 | Barra et al. | 606/108 |
| 5,830,222 | 11/1998 | Makower | 606/159 |
| 5,830,228 | 11/1998 | Knapp et al. | 606/195 |
| 5,779,731 | 07/1998 | Leavitt | 606/194 |
| 5,766,158 | 06/1998 | Opolski | 604/265 |
| 5,732,872 | 03/1998 | Bolduc et al. | 227/176.1 |
| 5,695,504 | 12/1997 | Gifford, III et al. | 606/153 |
| 5,662,700 | 09/1997 | Lazarus | 623/1 |
| 5,662,580 | 09/1997 | Bradshaw et al. | 600/3 |
| 5,634,936 | 06/1997 | Linden et al. | 606/213 |
| 5,620,649 | 04/1997 | Trotta | 264/515 |
| 5,616,114 | 04/1997 | Thornton et al. | 600/3 |
| 5,613,979 | 05/1997 | Trotta et al. | 606/194 |
| 5,522,834 | 06/1996 | Fonger et al. | 606/194 |

UNITED STATES PATENT AND TRADEMARK OFFICE
CERTIFICATE OF CORRECTION

PATENT NO.        : 6,626,921 B2
APPLICATION NO. : 10/003956
DATED             : September 30, 2003
INVENTOR(S)      : Blatter et al.

It is certified that error appears in the above-identified patent and that said Letters Patent is hereby corrected as shown below:

| | | | |
|---|---|---|---|
| 5,478,354 | 12/1995 | Tovey et al. | 606/219 |
| 5,478,320 | 12/1995 | Trotta | 604/96 |
| 5,456,712 | 10/1995 | Maginot | 623/1 |
| 5,411,475 | 05/1995 | Atala et al. | 604/54 |
| 5,366,462 | 11/1994 | Kaster et al. | 606/153 |
| 5,336,233 | 08/1994 | Chen | 606/153 |
| 5,290,306 | 03/1994 | Trotta et al. | 606/194 |
| 5,254,113 | 10/1993 | Wilk | 606/8 |
| 5,222,970 | 06/1993 | Reeves | 606/195 |
| 5,047,039 | 09/1991 | Avant et al. | 606/148 |
| 5,035,702 | 07/1997 | Taheri | 606/153 |
| 4,930,674 | 06/1990 | Barak | 227/179 |
| 4,917,091 | 04/1990 | Berggren et al. | 606/153 |
| 4,917,090 | 04/1990 | Berggren et al. | 606/153 |
| 4,917,087 | 04/1990 | Walsh et al. | 606/153 |
| 4,907,591 | 03/1990 | Vasconcellos et al. | 606/154 |
| 4,873,977 | 10/1989 | Avant et al. | 128/334 |
| 4,861,336 | 08/1989 | Helzel | 604/53 |
| 4,848,367 | 07/1989 | Avant et al. | 128/898 |
| 4,846,186 | 07/1989 | Box et al. | 128/657 |
| 4,819,637 | 04/1989 | Dormandy, Jr. et al. | 128/325 |
| 4,721,109 | 01/1988 | Healey | 128/334 |
| 4,657,019 | 04/1987 | Walsh et al. | 128/334 |
| 4,607,637 | 08/1986 | Berggren et al. | 128/334 |
| 4,553,542 | 11/1985 | Schenck et al. | 128/334 |
| 4,523,592 | 06/1985 | Daniel | 128/334 |
| 4,493,321 | 01/1985 | Leather | 128/305 |
| 4,366,819 | 01/1983 | Kaster | 128/334 |
| 3,258,012 | 06/1966 | Nakayama et al. | 128/334 |
| 3,254,650 | 06/1966 | Collito | 128/334 |
| 2,434,030 | 01/1948 | Yeomans | 128/346 |

UNITED STATES PATENT AND TRADEMARK OFFICE
CERTIFICATE OF CORRECTION

PATENT NO.       : 6,626,921 B2
APPLICATION NO.  : 10/003956
DATED            : September 30, 2003
INVENTOR(S)      : Blatter et al.

It is certified that error appears in the above-identified patent and that said Letters Patent is hereby corrected as shown below:

FOREIGN PATENT DOCUMENTS

| WO | WO 99/11180 | 03/1999 |
| WO | WO 98/19634 | 05/1998 |
| WO | WO 98/19629 | 05/1998 |
| WO | WO 98/06356 | 02/1998 |
| WO | WO 97/12555 | 04/1997 |
| WO | WO 93/00868 | 01/1993 |

OTHER PUBLICATIONS

Boeckx, Willy D. MD, PhD, Scanning Electron Microscopic Analysis of the Stapled Microvascular Anastomosis in the Rabbit, http://198.76.172.231/cgi-bin/bio/con/annals/atseq/63/S128/1997/ALL, Ann Thorac Surg, 1997, pp. 63:S128-34

Boeckx, Willy D. MD, PhD, et al., Scanning Electron Microscopic Analysis of the Stapled Microvasuclar Anastomosis in the Rabbit, Ann Thorac Surg, 1997, pp. 63:S128-34.

Borst, Cornelius MD, Ph.D, et al., Minimally Invasive Coronary Artery Bypass Grafting: On the Beating Heart and via Limited Access, Ann Thorac Surg, 1997, pp. S1-S5.

Brittinger, Wolf Dieter et al., Vascular Access for Hemodialysis in Children, Pediatric Nephrology, 1997, pp. 11:87-95.

Cecchetti, W., et al., 980nm High Power Diode Laser in Surgical Applications, Biomedical Optical Instrumentation and Laser-Assisted Biotechnology, 1996, pp. 227-230.

Chikamatsu, Eiji MD, et al., Comparison of Laser Vascular Welding, Interrupted Sutures, and Continuous Sutures in Growing Vascular Anastomoses, Lasers in Surgery and Medicine, Vol. 16, No. 1, 1995 pp. 34-40.

Cooley, Brian C. MD, Heat-induced Tissue Fusion for Microvascular Anastomosis, Microsurgery, Vol. 17, No. 4, 1996, pp. 198-208.

UNITED STATES PATENT AND TRADEMARK OFFICE
CERTIFICATE OF CORRECTION

PATENT NO.      : 6,626,921 B2
APPLICATION NO. : 10/003956
DATED           : September 30, 2003
INVENTOR(S)     : Blatter et al.

It is certified that error appears in the above-identified patent and that said Letters Patent is hereby corrected as shown below:

Cope, Constantin and Stanley Baum, Catheters, Methods, and Injectors for Superselective Catheterization, Abrams' Angiography Vascular and Interventional Radiology, Vol. 1, Fourth Edition, pp. 155-165.

D'Amelio, Frank D. et al., Fiber Optic Angioscopes, Novel Optical Fiber Techniques for Medical Applications, Vol. 494, Aug. 21, 1984, pp. 44-51.

Deckelbaum, Lawrence I. MD, Cardiovascular Applications of Laser Technology, Laser Surgery and Medicine Principles and Practice, 1996, pp. 1-27.

Dumanian, G.A. MD et al., A New Photopolymerizable Blood Vessel Glue That Seals Human Vessel Anastomoses Without Augmenting Thrombogenicity, Plastic and Reconstructive Surgery, Vol. 95, No. 5, April 1995, pp. 901-907.

Dumitras, D.C.D.C.A. DUTU, Surgical Properties and Applications of Sealed-Off $CO_2$ Lasers, Biomedical Optical Instrumentation and Laser-Assisted Biotechnology, 1996, pp. 231-239.

Falciai, R. et al., Ocide Glass Hollow Fiber for $CO_2$ Laser Radiation Transmission, Novel Optical Fiber Techniques for Medical Applications, Vol. 494, Aug. 21, 1984, pp. 84-87.

Gershony, Gary MD et al., Novel Vascular Sealing Device for Closure of Percutaneous Vascular Access Sites, Catherization and Cardiovascular Diagnosis, Sept. 1998, pp. 82-88.

Giele, Henk M.B.B.S., Histoacryl Glue as a Hemostatic Agent in Microvascular Anastomoses, Plastic and Reconstructive Surgery, Vol. 94, No. 6, Nov. 1994, p. 897.

Goldman, Leon and W.A. Taylor, Development of a Laser Intravascular Fiber Optic Probe for the Treatment of Superficial Telangiectasia of the Lower Extremity in Man, Novel Optical Fiber Techniques for Medical Application, Vol. 494, Aug. 21, 1984, pp. 76-84.

Gray, John L. MD et al., FGF-1 Affixation Stimulates ePTFE Endothelialization without Intimal Hyperplasia[1-2], Journal of Surgical Research Clinical and Laboratory Investigation, Vol. 57, No. 5, Nov. 1994, pp. 596-612.

UNITED STATES PATENT AND TRADEMARK OFFICE
CERTIFICATE OF CORRECTION

PATENT NO. : 6,626,921 B2
APPLICATION NO. : 10/003956
DATED : September 30, 2003
INVENTOR(S) : Blatter et al.

It is certified that error appears in the above-identified patent and that said Letters Patent is hereby corrected as shown below:

Greisler, Howard P. et al., Biointeractive Polymers and Tissue Engineered Blood Vessels, Biomaterials, Vol. 17, No. 3, Feb. 1996, pp. 329-336.

Han, Seung-kyu MD, PhD et al., Microvascular Anastomosis with Minimal Suture and Fibrin Glue: Experimental and Clinical Study, Microsurgery, Vol. 18, No. 5, 1998, pp. 306-311.

Haruguchi, Hiroaki et al., Clinical Application of Vascular Closure Staple Clips for Blood Access Surgery, ASAIO Journal, Sept.-Oct. 1998, pp. M562-564.

Humar, Abhinav MD et al., The Acutely Ischemic Extremity After Kidney Transplant: An Approach to Management, Surgery, March 1998, pp. 344-350.

Jaber, Saad F. MD et al., Role of Flow Measurement Technique in Anastomotic Quality Assessment in Minimally Invasive CABG, Ann Thorac Surg, 1998, pp. 66:1087-92.

Jones, Jon W. MD, A New Anastomotic Technique in Renal Transplants Reduces Warm Ischemia Time, Clinical Transplantation, 1998, 12:70-78.

Jules S. Scheltes, Msc, et al., Assessment of Patented Coronary End-to-side Anastomotic Devices Using Micromechanical Bonding, Ann Thorac Surg, 2000, pp. 218-221.

Keskil, S. et al., Early Phase Early Phase Alterations, in Endothelium Dependent Vasorelaxation Responses Due to Aneurysm Clip Application and Related Manipulations, The European Journal of Neurosurgery, Vol. 139, No. 1, 1997, pp. 71-76.

Kirschner, R.A. The Nd:YAG Laser – Applications in Surgery, Laser Systems for Photobiology and Photomedicine, 1991, pp. 53-56.

Kung, Robert T.V. PhD et al., Absorption Characteristics at 1.p µm: Effect on Vascular Welding, Lasers in Surgery and Medicine, Vol. 13, No. 1, 1993, pp 12-17.

Lanzetta, M. MD, et al., Fibroblast Growth Factor Pretreatment of 1-MM PTFE Grafts, Microsurgery, Vol. 17, No. 11, 1996, pp. 606-611.

UNITED STATES PATENT AND TRADEMARK OFFICE
CERTIFICATE OF CORRECTION

PATENT NO.         : 6,626,921 B2
APPLICATION NO. : 10/003956
DATED                 : September 30, 2003
INVENTOR(S)       : Blatter et al.

It is certified that error appears in the above-identified patent and that said Letters Patent is hereby corrected as shown below:

Ling Zhang, et al., Venous Microanastomosis with the Unilink System, Sleeve, and Suture Techniques: A Comparative Study in the Rat, Journal of Reconstructive Microsurgery, Vol. 13, No. 4, May 1997, pp. 257-262.

Lisi, Gianfranco MD et al., Nonpenetrating Stapling: A Valuable Alternative for Coronary Anastomoses? A Comparative Study in the Rat, Journal of Reconstructive Microsurgery, Vol. 13, No. 4, May 1997, pp. 257-262.

Marek, Christopher A., BS et al., Acute Thrombogenic Effects of Fibrin Sealant on Microvascular Anastomoses in a Rat Model, Annals of Plastic Surgery, Oct, 1998, pp. 415-419.

Menovsky, Thomas MD et al., Use of Fibrin Glue to Protect Tissue During $Co_2$ Laser Surgery, The Laryngoscope, Vol. 108, No. 9, pp. 1390-1393.

Mignani, A.G. and A.M. Scheggi, The Use of Optical Fibers in Biomedical Sensing, Laser Systems for Photobiology and Photomedicine, 1991, pp. 233-245.

Nataf, Patrick MD et al., Facilitated Vascular Anastomoses: The One Shot Device, Ann of Thorac Surg, 1998, pp. 66:1041-1044.

Nataf, Patrick MD, et al., Nonpenetrating Clips for Coronary Anastomosis, Ann Thorac Surg, 1997, pp. 63:S135-7.

Nataf, Patrick MD, et al., Nonpenetrating Clips for Coronary Anastomosis, http://198.76.172.231/cgi-bin/bio/con/annals/atseq/63/S135/1997/ALL, Ann of Thorac Surg, 1997, pp. 63:S135-137.

Nelson, Christine C. MD, et al., Eye Shield for patients Undergoing Laser Treatment, American Journal of Ophthalmology, Series 3, Vol. 110, No. 1, July 1990, pp. 39-43.

Neimz, Markolf H. References, Laser-Tissue Interactions – Fundamentals and Applications, Springer, 1996, pp. 267-290.

Niemz, Markolf H. Interaction Mechanisms, Laser-tissue Interactions – Fundamentals and Applications, Springer 1996, pp. 45-47.

Niemz, Markolf H. Lasers in Angioplasty and Cardiology, Laser-Tissue Interactions – Fundamentals and Applications, Springer, 1996, pp. 216-221.

UNITED STATES PATENT AND TRADEMARK OFFICE
CERTIFICATE OF CORRECTION

PATENT NO.       : 6,626,921 B2
APPLICATION NO.  : 10/003956
DATED            : September 30, 2003
INVENTOR(S)      : Blatter et al.

It is certified that error appears in the above-identified patent and that said Letters Patent is hereby corrected as shown below:

Papalois, V.E. et al., Use of Vascular Closure Staples in Vascular Access for Dialysis, Kidney and Pancreas Transplantation, International Surgery, April-June 1998, pp. 177-180.

Perkins, Rodney MD, Lasers in Medicine, Lasers Invention to Application, 1987, pp. 101-110.

Piano, Giancarlo MD et al., Assessing Outcomes, Costs, and Benefits of Emerging Technology for Minimally Invasive Saphenous Vein In Situ Distal Arterial Bypasses, Archives of Surgery, June 1998, pp. 613-618.

Pikoulis, Emmanouil MD, et al., Rapid Arterial Anastomosis with Titanium Clips, The American Journal of Surgery, June 1998, pp. 494-496.

Poppas, Dix P. MD et al., Preparation of Human Albumin Solder for Laser Tissue Welding, Laser in Surgery and Medicine, Vol. 13, No. 5, 1993, pp. 577-580.

Reardon, M. J. et al., Coronary Artery Bypass Conduits: Review of Current Status, The Journal of Cardiovascular Surgery, June 1997, pp. 201-209.

Reichenspurner, Hermann MD, PhD et al., Minimally Invasive Coronary Artery Bypass Grafting: Port-Access Approach Versus Off-Pump Techniques, Ann of Thorac Surg, 1998, pp. 66:1036-1040.

Rouhi, A. Maureen, Contemporary Biomaterials, Chemical & Engineering News, Vol. 77, No. 3, Jan, 1999, pp. 51-63.

Russel, D.A. et al., A Comparison of Laser and Arc-Lamp Spectroscopic Systems for In-Vivo Pharmacokinetic Measurements of Photosensitizers Used in Photodynamic Therapy, Laser Systems for Photobiology and Photomedicine, 1991, 193-199.

Saitoh, Satoru MD and Yudio Nakatsuchi MD, Telescoping and Glue Technique in Vein Grafts for Arterial Defects, Plastic and Reconstructive Surgery, Vol. 96, No. 6, Nov. 1995, pp. 1401-1408.

UNITED STATES PATENT AND TRADEMARK OFFICE
CERTIFICATE OF CORRECTION

PATENT NO.       : 6,626,921 B2
APPLICATION NO.  : 10/003956
DATED            : September 30, 2003
INVENTOR(S)      : Blatter et al.

It is certified that error appears in the above-identified patent and that said Letters Patent is hereby corrected as shown below:

Sanborn, Timothy A. Laser Angioplasty, Vascular Medicine A Textbook of Vascular Biology and Diseases, pp. 771-787.

Schnapp, Lynn M. MD, Elmer's Glue, Elsie and You: Clinical Applications of Adhesion Molecules, The Mount Sinai Journal of Medicine, May 1998, pp. 224-231.

Self, Steven B. MD et al., Limited Thrombogenicity of Low Temperature, Laser-Welded Vascular Anastomoses, Lasers in Surgery and Medicine, Vol. 18, No. 3, 1996, pp. 241-247.

Shennib, Hani MD et al., Computer-Assisted Telemanipulation: An Enabling Technology for Endoscopic Coronary Artery Bypass, Ann Thorac Surg 1998, pp. 66:1060-3.

Shindo, Maisie L. MD et al., Use of a Mechanical Microvascular Anastomotic Device in Head and Neck Free Tissue Transfer, Archives of Otolaryngology-Head & Neck Surgery, May, 1996, pp. 529-532.

Shinoda, Toshiharu MD et al., Creation of Viable Pulmonary Artery Autografts Through Tissue Engineering, The Journal of Thoracic and Cardiovascular Surgery, March 1998, pp. 536-546.

Spinelli, P. et al., Endoscopic Photodynamic Therapy: Clinical Aspects, Laser Systems for Photobiology and Photomedicine, 1991, pp. 149-155.

Stephenson, Jr., Edward R MD et al., Robotically Assisted Microsurgery for Endoscopic Coronary Artery Bypass Grafting, Ann of Thorac Surg, 1998, pp. 66:1064-1067.

Tulleken, Cornelis A. F. MD PhD et al., Nonocclusive Excimer Laser-Assisted End-to-Side Anastomosis, Ann Thorac Surg, 1997, pp. 63:S138-42.

Tulleken, Cornelis A. F. MD, PhD, et al., Nonocclusive Excimer Laser-Assisted End-to-Side Anastomosis, http://198.76.172.231/cgi-bin/bio/con/annals/atseq/63/S138/1997/ALL, Ann Thorac Surg, 1997, pp. 63:S138-42.

UNITED STATES PATENT AND TRADEMARK OFFICE
CERTIFICATE OF CORRECTION

PATENT NO. : 6,626,921 B2
APPLICATION NO. : 10/003956
DATED : September 30, 2003
INVENTOR(S) : Blatter et al.

It is certified that error appears in the above-identified patent and that said Letters Patent is hereby corrected as shown below:

Turi, Zoltan G., MD et al., Plugging the Artery With a Suspension: A Cautious Appraisal, Catherization and Cardiovascular Diagnosis, Sept. 1998, pp. 95-102.

Underwood, M.J. et al., Autogenous Arterial Grafts for Coronary Bypass Surgery: Current Status and Future Perspectives, International Journal of Cardiology 46, 1994, pp. 95-102.

Viligiardi, R. et al., Excimer Laser Angioplasty in Human Artery Disease, Laser Systems for Photobiology and Photomedicine, 1991, pp. 69-72.

Web Page, http://198.76.172.231/cgi-bin/bio/con/annuals/atseq/63/S122/1997 figs./5081f6,The Microvascular Anastomotic System as marketed by the Medical-Surgical Division of 3M Health Care, The Society of Thoracic Surgeons, 1997.

Weinschelbaum, Ernesto MD et al., Left Anterior Descending Coronary Artery Bypass Grafting Through Minimal Thoracotomy, Ann Thoracic Surg, 1998, pp. 66:1008-11.

Werker, Paul M. N. MD, Ph.D, et al., Review of Facilitated Approaches to Vascular Anastomosis Surgery, Ann Thorac Surg; 1997, pp. S122—S127.

Zarge, Joseph I. MD et al., Fibrin Glue Containing Fibroblast Growth Factor Type 1 and Heparin Decreased Platelet Deposition, The American Journal of Surgery; August 1997, pp. 188-192.

UNITED STATES PATENT AND TRADEMARK OFFICE
CERTIFICATE OF CORRECTION

PATENT NO.       : 6,626,921 B2
APPLICATION NO.  : 10/003956
DATED            : September 30, 2003
INVENTOR(S)      : Blatter et al.

It is certified that error appears in the above-identified patent and that said Letters Patent is hereby corrected as shown below:

Column 12, line 57, ". . . has been inserted though the wall. . ." change to --has been inserted through the wall--

Signed and Sealed this

Third Day of June, 2008

JON W. DUDAS
*Director of the United States Patent and Trademark Office*